United States Patent
Kubota et al.

(10) Patent No.: US 10,079,344 B2
(45) Date of Patent: Sep. 18, 2018

(54) ASYMMETRIC MONOANTHRACENE DERIVATIVE, MATERIAL FOR ORGANIC ELECTROLUMINESCENT DEVICE AND ORGANIC ELECTROLUMINESCENT DEVICE UTILIZING THE SAME

(71) Applicant: IDEMITSU KOSAN CO., LTD., Chiyoda-ku (JP)

(72) Inventors: Mineyuki Kubota, Sodegaura (JP); Masakazu Funahashi, Sodegaura (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 270 days.

(21) Appl. No.: 14/742,062

(22) Filed: Jun. 17, 2015

(65) Prior Publication Data

US 2015/0287928 A1   Oct. 8, 2015

Related U.S. Application Data

(60) Division of application No. 14/021,769, filed on Sep. 9, 2013, now abandoned, which is a continuation of application No. 10/572,586, filed as application No. PCT/JP2004/018111 on Nov. 30, 2004, now Pat. No. 8,568,902.

(30) Foreign Application Priority Data

Dec. 1, 2003  (JP) .................. 2003-401038

(51) Int. Cl.
| | |
|---|---|
| C07C 13/573 | (2006.01) |
| H01L 51/00 | (2006.01) |
| C07C 15/28 | (2006.01) |
| C09K 11/06 | (2006.01) |
| H05B 33/14 | (2006.01) |
| C07C 15/30 | (2006.01) |
| C07C 15/38 | (2006.01) |
| H01L 51/50 | (2006.01) |

(52) U.S. Cl.
CPC ........ *H01L 51/0058* (2013.01); *C07C 13/573* (2013.01); *C07C 15/28* (2013.01); *C07C 15/30* (2013.01); *C07C 15/38* (2013.01); *C09K 11/06* (2013.01); *H01L 51/0052* (2013.01); *H05B 33/14* (2013.01); *C07C 2603/24* (2017.05); *C07C 2603/26* (2017.05); *C07C 2603/50* (2017.05); *C09K 2211/1007* (2013.01); *C09K 2211/1011* (2013.01); *C09K 2211/1014* (2013.01); *C09K 2211/1048* (2013.01); *H01L 51/006* (2013.01); *H01L 51/0059* (2013.01); *H01L 51/0081* (2013.01); *H01L 51/5012* (2013.01); *H01L 2251/308* (2013.01)

(58) Field of Classification Search
CPC .................. H01L 51/0058; C07C 13/57
See application file for complete search history.

(56) References Cited

U.S. PATENT DOCUMENTS

| | | | |
|---|---|---|---|
| 5,536,949 A | 7/1996 | Hosokawa et al. | |
| 7,056,601 B2 | 6/2006 | Cosimbescu et al. | |
| 7,504,526 B2 | 3/2009 | Kubota et al. | |
| 7,517,592 B2 * | 4/2009 | Igarashi ................. | C07C 13/62 257/40 |
| 8,568,902 B2 * | 10/2013 | Kubota ................. | C07C 13/573 313/504 |
| 2002/0132134 A1 | 9/2002 | Hu et al. | |
| 2005/0089715 A1 | 4/2005 | Cosimbescu et al. | |
| 2007/0055085 A1 | 3/2007 | Kubota et al. | |
| 2007/0152565 A1 | 7/2007 | Kubota et al. | |
| 2009/0200929 A1 | 8/2009 | Kubota et al. | |

FOREIGN PATENT DOCUMENTS

| | | |
|---|---|---|
| EP | 1 182 183 | 2/2002 |
| EP | 1 333 018 | 8/2003 |
| EP | 1 533 289 A1 | 5/2005 |
| JP | 3-200889 | 9/1991 |
| JP | 7-138561 | 5/1995 |
| JP | 8-12600 | 1/1996 |
| JP | 8-239655 | 9/1996 |
| JP | 11-3762 | 1/1999 |
| JP | 2000-182776 | 6/2000 |
| JP | 2000-273056 | 10/2000 |
| JP | 2001-257074 | 9/2001 |
| JP | 2003-267472 | 9/2003 |
| JP | 2003261472 | * 9/2003 |
| JP | 2003-338375 | 11/2003 |
| WO | WO 03/080559 A1 | 10/2003 |
| WO | WO 03/087023 A1 | 10/2003 |
| WO | 2005/042667 | 5/2005 |

OTHER PUBLICATIONS

Ried et al., Diene syntheses with diynes Chemische Berichte (1960), 93, 1769-73.*

(Continued)

*Primary Examiner* — Paul V Ward
(74) *Attorney, Agent, or Firm* — Oblon, McClelland, Maier & Neustadt, L.L.P.

(57) ABSTRACT

Provided are an asymmetric monoanthracene derivative having a specific structure, a material for an organic EL device comprising the above asymmetric monoanthracene derivative and an organic EL device in which an organic thin film layer comprising a single layer or plural layers including a luminescent layer is interposed between a cathode and an anode, wherein at least one of the above organic thin film layers contains the asymmetric monoanthracene derivative described above in the form of a single component or a mixed component. Provided are an organic electroluminescent (EL) device having a high luminous efficiency and a long life, an asymmetric monoanthracene derivative which materializes the same and a material for an organic EL device.

18 Claims, No Drawings

(56) References Cited

OTHER PUBLICATIONS

U.S. Appl. No. 11/608,967, filed Dec. 11, 2006, Kubota, et al.
C. W. Tang, et al., "Organic Electroluminescent Diodes", Applied Physic Letters, vol. 51, No. 12, Sep. 21, 1987, pp. 913-915.
C. W. Tang, et al., "Organic Electroluminescent Diodes", Applied Physics Letters, vol. 51, No. 12, Sep. 21, 1987, pp. 913-915.
Extended European Search Report dated May 11, 2012, in Patent Application No. 12151549.8.

* cited by examiner

ASYMMETRIC MONOANTHRACENE DERIVATIVE, MATERIAL FOR ORGANIC ELECTROLUMINESCENT DEVICE AND ORGANIC ELECTROLUMINESCENT DEVICE UTILIZING THE SAME

CROSS-REFERENCE TO RELATED APPLICATIONS

The present application is a divisional application of U.S. application Ser. No. 14/021,769, pending, which is a continuation of U.S. application Ser. No. 10/572,586, now U.S. Pat. No. 8,568,902, which is a national stage application of PCT/JP04/18111 having a filing date of Nov. 30, 2004 and claiming priority to Japanese Application No. 2003/401038 having a filing date of Dec. 1, 2003.

TECHNICAL FIELD

The present invention relates to an asymmetric monoanthracene derivative, a material for an organic electroluminescent device and an organic electroluminescent device making use of it, more specifically to an organic electroluminescent device having a high luminous efficiency and a long life, an asymmetric monoanthracene derivative which materializes the same and a material for an organic electroluminescent device.

BACKGROUND ART

An organic electroluminescent device (hereinafter "electroluminescent" shall be abbreviated as EL) is a spontaneous luminescent device making use of the principle that a fluorescent substance emits light by recombination energy of holes injected from an anode and electrons injected from a cathode by applying an electric field. Since a low voltage-driven organic EL device of a laminate type was reported by C. W. Tang of Eastman Kodak Company (C. W. Tang and S. A. Vanslyke, Applied Physics Letters, Vol. 51, p. 913, 1987), researches on organic EL devices comprising organic materials as structural materials have actively been carried out. Tang et al. use tris(8-hydroxyquinolinolaluminum) for the luminescent layer and a triphenyldiamine derivative for the hole transporting layer. The advantages of a laminate structure include an elevation in an efficiency of injecting holes into a luminescent layer, a rise in a forming efficiency of excitons formed by blocking electrons injected from a cathode to recombine them and shutting up of excitons formed in the luminescent layer. As shown in the above example, a two layer type comprising a hole transporting (injecting) layer and an electron transporting and luminescent layer and a three layer type comprising a hole transporting (injecting) layer, a luminescent layer and an electron transporting (injecting) layer are well known as the device structures of the organic EL device. In such laminate type structural devices, device structures and forming methods are studied in order to enhance a recombination efficiency of holes and electrons injected.

Known as luminescent materials are luminescent materials such as chelate complexes such as a tris(8-quinolinolate) aluminum complex, coumarin derivatives, tetraphenylbutadiene derivatives, bisstyrylarylene derivatives and oxadiazole derivatives. It is reported that luminescence of a blue color to a red color in a visible region is obtained from them, and it is expected that a color display device is materialized (for example, patent document 1, patent document 2 and patent document 3).

Further, a device using a phenylanthracene derivative as a luminescent material is disclosed in patent document 4. Such anthracene derivative is used as a blue color luminescent material, and it has been desired to extend the device life. A material having a naphthyl group in 9 and 10 positions of anthracene is disclosed in patent document 5, and a material having a fluoranthene group in 9 and 10 positions of anthracene is disclosed in patent document 6. These anthracene derivatives are also used as a blue color luminescent material, and it has been desired as well to improve the device life. Further, it is disclosed in patent document 7 to use various anthracene derivatives as a hole transporting material. However, they have not yet been evaluated as a luminescent material.

[Patent document 1]: Japanese Patent Application Laid-Open No. 239655/1996

[Patent document 2]: Japanese Patent Application Laid-Open No. 138561/1995

[Patent document 3]: Japanese Patent Application Laid-Open No. 200289/1991

[Patent document 4]: Japanese Patent Application Laid-Open No. 012600/1996

[Patent document 5]: Japanese Patent Application Laid-Open No. 3782/1999

[Patent document 6]: Japanese Patent Application Laid-Open No. 257074/2001

[Patent document 7]: Japanese Patent Application Laid-Open No. 182776/2000

DISCLOSURE OF THE INVENTION

The present invention has been made in order to solve the problems described above, and an object thereof is to provide an organic EL device having a high luminous efficiency and a long life, an asymmetric monoanthracene derivative which materializes the same and a material for an organic EL device.

Intensive researches repeated by the present inventors in order to achieve the object described above have resulted in finding that if a compound having a specific monoanthracene structure of an asymmetric type represented by Formula (1) shown below is used as a luminescent material in an organic EL device, the organic EL device having a high luminous efficiency and a long life is obtained, and thus they have come to complete the present invention. Further, use of the compound having a specific monoanthracene structure of an asymmetric type represented by Formula (1) shown below makes it possible to lower a depositing temperature of the compound and inhibits the compound from being thermally decomposed in deposition.

That is, the present invention provides an asymmetric monoanthracene derivative represented by Formula (1) shown below, a material for an organic EL device comprising the above asymmetric monoanthracene derivative and an organic EL device in which an organic thin film layer comprising a single layer or plural layers including a luminescent layer is interposed between a cathode and an anode, wherein at least one of the above organic thin film layers contains the asymmetric monoanthracene derivative represented by Formula (1) in the form of a single component or a mixed component:

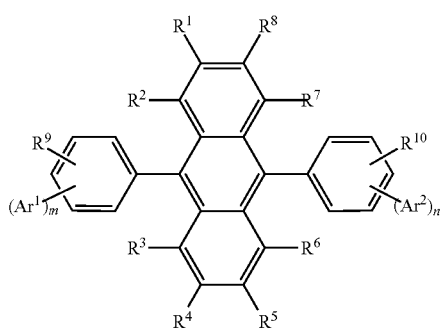

(1)

wherein $Ar^1$ and $Ar^2$ each are independently a substituted or non-substituted aromatic hydrocarbon ring group having 6 to 50 nuclear carbon atoms, and m and n each are an integer of 1 to 4, provided that when m and n are 1 and the bonding positions of $Ar^1$ and $Ar^2$ in the benzene rings are symmetric in right and left, $Ar^1$ is not the same as $Ar^2$ and that when m or n is an integer of 2 to 4, m and n are different integers.

$R^1$ to $R^8$ each are independently a hydrogen atom, a substituted or non-substituted aromatic hydrocarbon ring group having 6 to 50 nuclear carbon atoms, a substituted or non-substituted aromatic heterocyclic group having 5 to 50 nuclear atoms, a substituted or non-substituted alkyl group having 1 to 50 carbon atoms, a substituted or non-substituted cycloalkyl group, a substituted or non-substituted alkoxy group having 1 to 50 carbon atoms, a substituted or non-substituted aralkyl group having 6 to 50 carbon atoms, a substituted or non-substituted aryloxy group having 5 to 50 nuclear atoms, a substituted or non-substituted arylthio group having 5 to 50 nuclear atoms, a substituted or non-substituted alkoxycarbonyl group having 1 to 50 carbon atoms, a substituted or non-substituted silyl group, a carboxyl group, a halogen atom, a cyano group, a nitro group or a hydroxyl group.

$R^9$ to $R^{10}$ each are independently a hydrogen atom, a substituted or non-substituted aromatic hydrocarbon ring group having 6 to 50 nuclear carbon atoms, a substituted or non-substituted alkyl group having 1 to 50 carbon atoms, a substituted or non-substituted cycloalkyl group, a substituted or non-substituted alkoxy group having 1 to 50 carbon atoms, a substituted or non-substituted aralkyl group having 6 to 50 carbon atoms, a substituted or non-substituted aryloxy group having 5 to 50 nuclear atoms, a substituted or non-substituted arylthio group having 5 to 50 nuclear atoms, a substituted or non-substituted alkoxycarbonyl group having 1 to 50 carbon atoms, a substituted or non-substituted silyl group, a carboxyl group, a halogen atom, a cyano group, a nitro group or a hydroxyl group, and any groups are not an alkenyl group.

Effect of the Invention

An organic EL device prepared by using the asymmetric monoanthracene derivative of the present invention as a material for the organic EL device has a high luminous efficiency and a long life.

BEST MODE FOR CARRYING OUT THE INVENTION

The asymmetric monoanthracene derivative of the present invention is represented by Formula (1) described above.

In Formula (1) described above, m and n each are an integer of 1 to 4, and they are preferably an integer of 1 to 2.

Provided that when m and n are 1 and the bonding positions of $Ar^1$ and $Ar^2$ in the benzene ring are symmetric in right and left, $Ar^1$ is not the same as $Ar^2$ and that when m or n is an integer of 2 to 4, m and n are different integers. In the present invention, the symmetric type in right and left means a case where when $Ar^1$ and $R^9$ are substituted in an $X^1$ position and an $X^2$ position in the benzene ring bonded to a 9 position of the anthracene ring, $Ar^2$ and $R^{10}$ also are substituted respectively in an $X^1$ position and an $X^2$ position in the benzene ring bonded to a 10 position of the anthracene ring.

That is, the anthracene derivative represented by Formula (1) assumes a structure in which the right and left benzene rings bonded to the anthracene ring and substituted with the aromatic hydrocarbon ring groups are asymmetric in right and left, and the anthracene derivative described above has an asymmetric structure.

For example, if substituents in a 2 position and a 3 position in the anthracene nucleus are different but substituents bonded to a 9 position and a 10 position are the same, it is not included in the asymmetric type defined in the present invention.

The derivative in which m and/or n are 1 in Formula (1) described above is more preferred, and when m is, for example, 1, the derivative represented by any of Formulas (2) to (4) is further preferred:

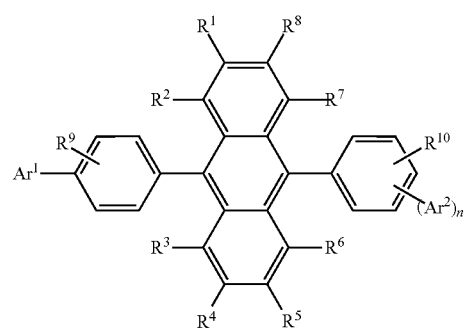

(2)

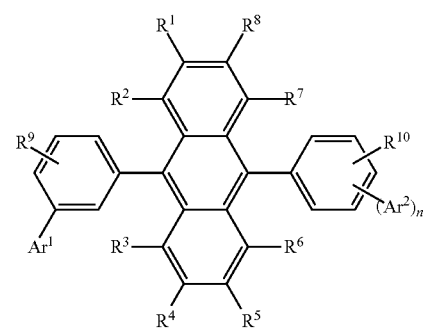

(3)

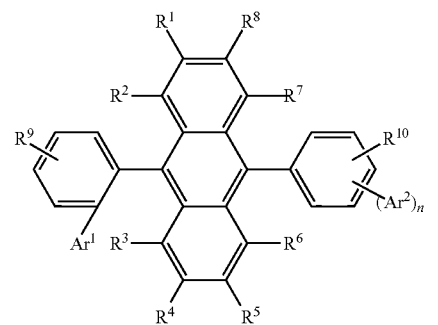

(4)

In Formulas (2) to (4), $Ar^1$, $Ar^2$, n and $R^1$ to $R^{10}$ are the same as in Formula (1).

As is the case with what was described above, in a case where n is 1 and the positions of $Ar^1$ and $Ar^2$ bonded to the benzene rings are symmetric in right and left, $Ar^1$ is not the same as $Ar^2$.

In Formula (1), $Ar^1$ and $Ar^2$ each are independently a substituted or non-substituted aromatic hydrocarbon ring group having 6 to 50 nuclear carbon atoms.

The substituted or non-substituted aromatic hydrocarbon ring group represented by $Ar^1$ and $Ar^2$ include, for example, phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 1-naphthacenyl, 2-naphthacenyl, 9-naphthacenyl, 1-pyrenyl, 2-pyrenyl, 4-pyrenyl, 2-biphenylyl, 3-biphenylyl, 4-biphenylyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-t-butylphenyl, p-(2-phenylpropyl)phenyl, 3-methyl-2-naphthyl, 4-methyl-1-naphthyl, 4-methyl-1-anthryl, 4'-methylbiphenylyl and 4"-t-butyl-p-terphenyl-4-yl.

Among them, preferred are phenyl, 1-naphthyl, 2-naphthyl, 9-phenanthryl, 1-naphthacenyl, 2-naphthacenyl, 9-naphthacenyl, 1-pyrenyl, 2-pyrenyl, 4-pyrenyl, 2-biphenylyl, 3-biphenylyl, 4-biphenylyl, o-tolyl, m-tolyl, p-tolyl and p-t-butylphenyl.

In Formula (1), $R^1$ to $R^8$ each are independently a hydrogen atom, a substituted or non-substituted aromatic hydrocarbon ring group having 6 to 50 nuclear carbon atoms, a substituted or non-substituted aromatic heterocyclic group having 5 to 50 nuclear atoms, a substituted or non-substituted alkyl group having 1 to 50 carbon atoms, a substituted or non-substituted cycloalkyl group, a substituted or non-substituted alkoxy group having 1 to 50 carbon atoms, a substituted or non-substituted aralkyl group having 6 to 50 carbon atoms, a substituted or non-substituted aryloxy group having 5 to 50 carbon atoms, a substituted or non-substituted arylthio group having 5 to 50 nuclear atoms, a substituted or non-substituted alkoxycarbonyl group having 1 to 50 carbon atoms, a substituted or non-substituted silyl group, a carboxyl group, a halogen atom, a cyano group, a nitro group or a hydroxyl group.

$R^9$ to $R^{10}$ each are independently a hydrogen atom, a substituted or non-substituted aromatic hydrocarbon ring group having 6 to 50 nuclear carbon atoms, a substituted or non-substituted alkyl group having 1 to 50 carbon atoms, a substituted or non-substituted cycloalkyl group, a substituted or non-substituted alkoxy group having 1 to 50 carbon atoms, a substituted or non-substituted aralkyl group having 6 to 50 carbon atoms, a substituted or non-substituted aryloxy group having 5 to 50 nuclear atoms, a substituted or non-substituted arylthio group having 5 to 50 nuclear atoms, a substituted or non-substituted alkoxycarbonyl group having 1 to 50 carbon atoms, a substituted or non-substituted silyl group, a carboxyl group, a halogen atom, a cyano group, a nitro group or a hydroxyl group, and any groups are not an alkenyl group.

The examples of the substituted or non-substituted aromatic hydrocarbon ring group represented by $R^1$ to $R^{10}$ include phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 1-naphthacenyl, 2-naphthacenyl, 9-naphthacenyl, 1-pyrenyl, 2-pyrenyl, 4-pyrenyl, 2-biphenylyl, 3-biphenylyl, 4-biphenylyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-t-butylphenyl, p-(2-phenylpropyl)phenyl, 3-methyl-2-naphthyl, 4-methyl-1-naphthyl, 4-methyl-1-anthryl, 4'-methylbiphenylyl and 4"-t-butyl-p-terphenyl-4-yl.

The examples of the substituted or non-substituted aromatic heterocyclic group represented by $R^1$ to $R^8$ include 1-pyrrolyl, 2-pyrrolyl, 3-pyrrolyl, pyrazinyl, 2-pyridinyl, 3-pyridinyl, 4-pyridinyl, 1-indolyl, 2-indolyl, 3-indolyl, 4-indolyl, 5-indolyl, 6-indolyl, 7-indolyl, 1-isoindolyl, 2-isoindolyl, 3-isoindolyl, 4-isoindolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 9-carbazolyl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthryldinyl, 1-acridinyl, 2-acridinyl, 3-acridinyl, 4-acridinyl, 9-acridinyl, 1,7-phenanthroline-2-yl, 1,7-phenanthroline-3-yl, 1,7-phenanthroline-4-yl, 1,7-phenanthroline-5-yl, 1,7-phenanthroline-6-yl, 1,7-phenanthroline-8-yl, 1,7-phenanthroline-9-yl, 1,7-phenanthroline-10-yl, 1,8-phenanthroline-2-yl, 1,8-phenanthroline-3-yl, 1,8-phenanthroline-4-yl, 1,8-phenanthroline-5-yl, 1,8-phenanthroline-6-yl, 1,8-phenanthroline-7-yl, 1,8-phenanthroline-9-yl, 1,8-phenanthroline-10-yl, 1,9-phenanthroline-2-yl, 1,9-phenanthroline-3-yl, 1,9-phenanthroline-4-yl, 1,9-phenanthroline-5-yl, 1,9-phenanthroline-6-yl, 1,9-phenanthroline-7-yl, 1,9-phenanthroline-8-yl, 1,9-phenanthroline-10-yl, 1,10-phenanthroline-2-yl, 1,10-phenanthroline-3-yl, 1,10-phenanthroline-4-yl, 1,10-phenanthroline-5-yl, 2,9-phenanthroline-1-yl, 2,9-phenanthroline-3-yl, 2,9-phenanthroline-4-yl, 2,9-phenanthroline-5-yl, 2,9-phenanthroline-6-yl, 2,9-phenanthroline-7-yl, 2,9-phenanthroline-8-yl, 2,9-phenanthroline-10-yl, 2,8-phenanthroline-1-yl, 2,8-phenanthroline-3-yl, 2,8-phenanthroline-4-yl, 2,8-phenanthroline-5-yl, 2,8-phenanthroline-6-yl, 2,8-phenanthroline-7-yl, 2,8-phenanthroline-9-yl, 2,8-phenanthroline-10-yl, 2,7-phenanthroline-1-yl, 2,7-phenanthroline-3-yl, 2,7-phenanthroline-4-yl, 2,7-phenanthroline-5-yl, 2,7-phenanthroline-6-yl, 2,7-phenanthroline-8-yl, 2,7-phenanthroline-9-yl, 2,7-phenanthroline-10-yl, 1-phenazinyl, 2-phenazinyl, 1-phenothiazinyl, 2-phenothiazinyl, 3-phenothiazinyl, 4-phenothiazinyl, 10-phenothiazinyl, 1-phenoxazinyl, 2-phenoxazinyl, 3-phenoxazinyl, 4-phenoxazinyl, 10-phenoxazinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrole-1-yl, 2-methylpyrrole-3-yl, 2-methylpyrrole-4-yl, 2-methylpyrrole-5-yl, 3-methylpyrrole-1-yl, 3-methylpyrrole-2-yl, 3-methylpyrrole-4-yl, 3-methylpyrrole-5-yl, 2-t-butylpyrrole-4-yl, 3-(2-phenylpropyl)pyrrole-1-yl, 2-methyl-1-indolyl, 4-methyl-1-indolyl, 2-methyl-3-indolyl, 4-methyl-3-indolyl, 2-t-butyl-1-indolyl, 4-t-butyl-1-indolyl, 2-t-butyl-3-indolyl and 4-t-butyl-3-indolyl.

The examples of the substituted or non-substituted alkyl group represented by $R^1$ to $R^{10}$ include methyl, ethyl, propyl, isopropyl, n-butyl, s-butyl, isobutyl, t-butyl, n-pentyl, n-hexyl, n-heptyl, n-octyl, hydroxymethyl, 1-hydroxyethyl, 2-hydroxyethyl, 2-hydroxyisobutyl, 1,2-dihydroxyethyl, 1,3-dihydroxyisopropyl, 2,3-dihydroxy-t-butyl, trihydroxypropyl, chloromethyl, 1-chloroethyl, 2-chloroethyl, 2-chloroisobutyl, 1,2-dichloroethyl, 1,3-dichloroisopropyl, 2,3-dichloro-t-butyl, 1,2,3-trichloropropyl, bromomethyl, 1-bromoethyl, 2-bromoethyl, 2-bromoisobutyl, 1,2-dibromoethyl, 1,3-dibromoisopropyl, 2,3-dibromo-t-butyl, 1,2,3-tribromopropyl, iodomethyl, 1-iodoethyl, 2-iodoethyl, 2-iodoisobutyl, 1,2-diiodoethyl, 1,3-diiodoisopropyl, 2,3-diiodo-t-butyl, 1,2,3-triiodopropyl, aminomethyl, 1-aminoethyl, 2-aminoethyl, 2-aminoisobutyl, 1,2-diaminoethyl, 1,3-diaminoisopropyl, 2,3-diamino-t-butyl, 1,2,3-triaminopropyl, cyanomethyl, 1-cyanoethyl, 2-cyanoethyl, 2-cyanoisobutyl, 1,2-dicyanoethyl, 1,3-dicyanoisopropyl, 2,3-dicyano-t-butyl, 1,2,3-tricyanopropyl, nitromethyl, 1-nitroethyl, 2-nitroethyl, 2-nitroisobutyl, 1,2-dinitroethyl, 1,3-dinitroisopropyl, 2,3-dinitro-t-butyl and 1,2,3-trinitropropyl.

The examples of the substituted or non-substituted cycloalkyl group represented by $R^1$ to $R^{10}$ include cyclopropyl, cyclobutyl, cyclopentyl, cyclohexyl, 4-methylcyclohexyl, 1-adamantyl, 2-adamantyl, 1-norbornyl and 2-norbornyl.

The substituted or non-substituted alkoxy group represented by $R^1$ to $R^{10}$ is a group represented by —OY, and the examples of Y include methyl, ethyl, propyl, isopropyl, n-butyl, s-butyl, isobutyl, t-butyl, n-pentyl, n-hexyl, n-heptyl, n-octyl, hydroxymethyl, 1-hydroxyethyl, 2-hydroxyethyl, 2-hydroxyisobutyl, 1,2-dihydroxyethyl, 1,3-dihydroxyisopropyl, 2,3-dihydroxy-t-butyl, 1,2,3-trihydroxypropyl, chloromethyl, 1-chloroethyl, 2-chloroethyl, 2-chloroisobutyl, 1,2-dichloroethyl, 1,3-dichloroisopropyl, 2,3-dichloro-t-butyl, 1,2,3-trichloropropyl, bromomethyl, 1-bromoethyl, 2-bromoethyl, 2-bromoisobutyl, 1,2-dibromoethyl, 1,3-dibromoisopropyl, 2,3-dibromo-t-butyl, 1,2,3-tribromopropyl, iodomethyl, 1-iodoethyl, 2-iodoethyl, 2-iodoisobutyl, 1,2-diiodoethyl, 1,3-diiodoisopropyl, 2,3-diiodo-t-butyl, 1,2,3-triiodopropyl, aminomethyl, 1-aminoethyl, 2-aminoethyl, 2-aminoisobutyl, 1,2-diaminoethyl, 1,3-diaminoisopropyl, 2,3-diamino-t-butyl, 1,2,3-triaminopropyl, cyanomethyl, 1-cyanoethyl, 2-cyanoethyl, 2-cyanoisobutyl, 1,2-dicyanoethyl, 1,3-dicyanoisopropyl, 2,3-dicyano-t-butyl, 1,2,3-tricyanopropyl, nitromethyl, 1-nitroethyl, 2-nitroethyl, 2-nitroisobutyl, 1,2-dinitroethyl, 1,3-dinitroisopropyl, 2,3-dinitro-t-butyl and 1,2,3-trinitropropyl.

The examples of the substituted or non-substituted aralkyl group represented by $R^1$ to $R^{10}$ include benzyl, 1-phenylethyl, 2-phenylethyl, 1-phenylisopropyl, 2-phenylisopropyl, phenyl-t-butyl, α-naphthylmethyl, 1-α-naphthylethyl, 2-α-naphthylethyl, 1-α-naphthylisopropyl, 2-α-naphthylisopropyl, β-naphthylmethyl, 1-β-naphthylethyl, 2-β-naphthylethyl, 1-β-naphthylisopropyl, 2-β-naphthylisopropyl, 1-pyrrolylmethyl, 2-(1-pyrrolyl)ethyl, p-methylbenzyl, m-methylbenzyl, o-methylbenzyl, p-chlorobenzyl, m-chlorobenzyl, o-chlorobenzyl, p-bromobenzyl, m-bromobenzyl, o-bromobenzyl, p-iodobenzyl, m-iodobenzyl, o-iodobenzyl, p-hydroxybenzyl, m-hydroxybenzyl, o-hydroxybenzyl, p-aminobenzyl, m-aminobenzyl, o-aminobenzyl, p-nitrobenzyl, m-nitrobenzyl, o-nitrobenzyl, p-cyanobenzyl, m-cyanobenzyl, o-cyanobenzyl, 1-hydroxy-2-phenylisopropyl and 1-chloro-2-phenylisopropyl.

The substituted or non-substituted aryloxy group represented by $R^1$ to $R^{10}$ is represented by —OY', and the examples of Y' include phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 1-naphthacenyl, 2-naphthacenyl, 9-naphthacenyl, 1-pyrenyl, 2-pyrenyl, 4-pyrenyl, 2-biphenylyl, 3-biphenylyl, 4-biphenylyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-t-butylphenyl, p-(2-phenylpropyl)phenyl, 3-methyl-2-naphthyl, 4-methyl-1-naphthyl, 4-methyl-1-anthryl, 4'-methylbiphenylyl, 4"-t-butyl-p-terphenyl-4-yl, 2-pyrrolyl, 3-pyrrolyl, pyrazinyl, 2-pyridinyl, 3-pyridinyl, 4-pyridinyl, 2-indolyl, 3-indolyl, 4-indolyl, 5-indonyl, 6-indolyl, 7-indolyl, 1-isoindolyl, 3-isoindolyl, 4-isoindolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthridinyl, 1-acridinyl, 2-acridinyl, 3-acridinyl, 4-acridinyl, 9-acridinyl, 1,7-phenanthroline-2-yl, 1,7-phenanthroline-3-yl, 1,7-phenanthroline-4-yl, 1,7-phenanthroline-5-yl, 1,7-phenanthroline-6-yl, 1,7-phenanthroline-8-yl, 1,7-phenanthroline-9-yl, 1,7-phenanthroline-10-yl, 1,8-phenanthroline-2-yl, 1,8-phenanthroline-3-yl, 1,8-phenanthroline-4-yl, 1,8-phenanthroline-5-yl, 1,8-phenanthroline-6-yl, 1,8-phenanthroline-7-yl, 1,8-phenanthroline-9-yl, 1,8-phenanthroline-10-yl, 1,9-phenanthroline-2-yl, 1,9-phenanthroline-3-yl, 1,9-phenanthroline-4-yl, 1,9-phenanthroline-5-yl, 1,9-phenanthroline-6-yl, 1,9-phenanthroline-7-yl, 1,9-phenanthroline-8-yl, 1,9-phenanthroline-10-yl, 1,10-phenanthroline-2-yl, 1,10-phenanthroline-3-yl, 1,10-phenanthroline-4-yl, 1,10-phenanthroline-5-yl, 2,9-phenanthroline-1-yl, 2,9-phenanthroline-3-yl, 2,9-phenanthroline-4-yl, 2,9-phenanthroline-5-yl, 2,9-phenanthroline-6-yl, 2,9-phenanthroline-7-yl, 2,9-phenanthroline-8-yl, 2,9-phenanthroline-10-yl, 2,8-phenanthroline-1-yl, 2,8-phenanthroline-3-yl, 2,8-phenanthroline-4-yl, 2,8-phenanthroline-5-yl, 2,8-phenanthroline-6-yl, 2,8-phenanthroline-7-yl, 2,8-phenanthroline-9-yl, 2,8-phenanthroline-10-yl, 2,7-phenanthroline-1-yl, 2,7-phenanthroline-3-yl, 2,7-phenanthroline-4-yl, 2,7-phenanthroline-5-yl, 2,7-phenanthroline-6-yl, 2,7-phenanthroline-8-yl, 2,7-phenanthroline-9-yl, 2,7-phenanthroline-10-yl, 1-phenazinyl, 2-phenazinyl, 1-phenothiazinyl, 2-phenothiazinyl, 3-phenothiazinyl, 4-phenothiazinyl, 1-phenoxazinyl, 2-phenoxazinyl, 3-phenoxazinyl, 4-phenoxazinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrole-1-yl, 2-methylpyrrole-3-yl, 2-methylpyrrole-4-yl, 2-methylpyrrole-5-yl, 3-methylpyrrole-1-yl, 3-methylpyrrole-2-yl, 3-methylpyrrole-4-yl, 3-methylpyrrole-5-yl, 2-t-butylpyrrole-4-yl, 3-(2-phenylpropyl)pyrrole-1-yl, 2-methyl-1-indolyl, 4-methyl-1-indolyl, 2-methyl-3-indolyl, 4-methyl-3-indolyl, 2-t-butyl-1-indolyl, 4-t-butyl-1-indolyl, 2-t-butyl-3-indolyl and 4-t-butyl-3-indolyl.

The substituted or non-substituted arylthio group represented by $R^1$ to $R^{10}$ is represented by —SY", and the examples of Y" include phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 1-naphthacenyl, 2-naphthacenyl, 9-naphthacenyl, 1-pyrenyl, 2-pyrenyl, 4-pyrenyl, 2-biphenylyl, 3-biphenylyl, 4-biphenylyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-t-butylphenyl, p-(2-phenylpropyl)phenyl, 3-methyl-2-naphthyl, 4-methyl-1-naphthyl, 4-methyl-1-anthryl, 4'-methylbiphenylyl, 4"-t-butyl-p-terphenyl-4-yl, 2-pyrrolyl, 3-pyrrolyl, pyrazinyl, 2-pyridinyl, 3-pyridinyl, 4-pyridinyl, 2-indolyl, 3-indolyl, 4-indolyl, 5-indolyl, 6-indolyl, 7-indolyl, 1-isoindolyl, 3-isoindolyl, 4-isoindolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthridinyl, 1-acridinyl, 2-acridinyl, 3-acridinyl, 4-acridinyl, 9-acridinyl, 1,7-phenanthroline-2-yl, 1,7-phenanthroline-3-yl, 1,7-phenanthroline-4-yl, 1,7-phenanthroline-5-yl, 1,7-phenanthroline-6-yl, 1,7-phenanthroline-8-yl, 1,7-phenanthroline-9-yl, 1,7-phenanthroline-10-yl, 1,8-phenanthroline-2-yl, 1,8-phenanthroline-3-yl, 1,8-phenanthroline-4-yl, 1,8-phenanthroline-5-yl, 1,8-phenanthroline-6-yl, 1,8-phenanthroline-7-yl, 1,8-phenanthroline-9-yl, 1,8-phenanthroline-10-yl, 1,9-phenanthroline-2-yl, 1,9-phenanthroline-3-yl, 1,9-phenanthroline-4-yl, 1,9-phenanthroline-5-yl, 1,9-phenanthroline-6-yl, 1,9-phenanthroline-7-yl, 1,9-phenanthroline-8-yl, 1,9-phenanthroline-10-yl, 1,10-phenanthroline-2-yl, 1,10-phenanthroline-3-yl, 1,10-phenanthroline-4-yl, 1,10-phenanthroline-5-yl, 2,9-phenanthroline-1-yl, 2,9-phenanthroline-3-yl, 2,9-phenanthroline-4-yl, 2,9-phenanthroline-5-yl, 2,9-phenanthroline-6-yl, 2,9-phenanthroline-7-yl, 2,9-phenanthroline-8-yl, 2,9-phenanthroline-10-yl, 2,8-phenanthroline-1-yl, 2,8-phenanthroline-3-yl, 2,8-phenanthroline-4-yl, 2,8-phenanthroline-5-yl, 2,8-phenanthroline-6-yl, 2,8-phenanthroline-7-yl, 2,8-phenanthroline-9-yl, 2,8-phenanthroline-10-yl, 2,7-phenanthroline-1-yl, 2,7-phenanthroline-3-yl, 2,7-phenanthroline-4-yl, 2,7-phenanthroline-5-yl, 2,7-phenanthroline-6-yl, 2,7-phenanthroline-8-yl, 2,7-phenanthroline-9-yl, 2,7-phenanthroline-10-yl, 1-phenazinyl, 2-phenazinyl, 1-phenothiazinyl, 2-phenothiazinyl, 3-phenothiazinyl, 4-phenothiazinyl, 1-phenoxazinyl, 2-phenoxazinyl, 3-phenoxazinyl, 4-phenoxazinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrole-1-yl, 2-methylpyrrole-3-yl, 2-methylpyrrole-4-yl, 2-methylpyrrole-5-yl, 3-methylpyrrole-1-yl, 3-methylpyrrole-2-yl, 3-methylpyrrole-4-yl, 3-methylpyrrole-5-yl, 2-t-butylpyrrole-4-yl, 3-(2-phenylpropyl)pyrrole-1-yl, 2-methyl-1-indolyl, 4-methyl-1-indolyl, 2-methyl-3-indolyl, 4-methyl-3-indolyl, 2-t-butyl-1-indolyl, 4-t-butyl-1-indolyl, 2-t-butyl-3-indolyl and 4-t-butyl-3-indolyl.

The substituted or non-substituted alkoxylcarbonyl group represented by $R^1$ to $R^{10}$ is represented by —COOZ, and the examples of Z include methyl, ethyl, propyl, isopropyl, n-butyl, s-butyl, isobutyl, t-butyl, n-pentyl, n-hexyl, n-heptyl, n-octyl, hydroxymethyl, 1-hydroxyethyl, 2-hydroxyethyl, 2-hydroxyisobutyl, 1,2-dihydroxyethyl, 1,3-dihydroxyisopropyl, 2,3-dihydroxy-t-butyl, 1,2,3-trihydroxypropyl, chloromethyl, 1-chloroethyl, 2-chloroethyl, 2-chloroisobutyl, 1,2-dichloroethyl, 1,3-dichloroisopropyl, 2,3-dichloro-t-butyl, 1,2,3-trichloropropyl, bromomethyl, 1-bromoethyl, 2-bromoethyl, 2-bromoisobutyl, 1,2-dibromoethyl, 1,3-dibromoisopropyl, 2,3-dibromo-t-butyl, 1,2,3-tribromopropyl, iodomethyl, 1-iodoethyl, 2-iodoethyl, 2-iodoisobutyl, 1,2-diiodoethyl, 1,3-diiodoisopropyl, 2,3-diiodo-t-butyl, 1,2,3-triiodopropyl, aminomethyl, 1-aminoethyl, 2-aminoethyl, 2-aminoisobutyl, 1,2-diaminoethyl, 1,3-diaminoisopropyl, 2,3-diamino-t-butyl, 1,2,3-triaminopropyl, cyanomethyl, 1-cyanoethyl, 2-cyanoethyl, 2-cyanoisobutyl, 1,2-dicyanoethyl, 1,3-dicyanoisopropyl, 2,3-dicyano-t-butyl, 1,2,3-tricyanopropyl, nitromethyl, 1-nitroethyl, 2-nitroethyl, 2-nitroisobutyl, 1,2-dinitroethyl, 1,3-dinitroisopropyl, 2,3-dinitro-t-butyl and 1,2,3-trinitropropyl.

The halogen atom represented by $R^1$ to $R^{10}$ includes fluorine, chlorine, bromine and iodine.

Substituents in the groups represented by $Ar^1$, $Ar^2$ and $R^1$ to $R^{10}$ each described above include a halogen atom, a hydroxyl group, a nitro group, a cyano group, an alkyl group, an aryl group, a cycloalkyl group, an alkoxy group, an aralkyl group, an aryloxy group, an arylthio group, an alkoxycarbonyl group or a carboxyl group.

The specific examples of the asymmetric monoanthracene derivative represented by Formula (1) in the present invention shall be shown below, but they shall not be restricted to these compounds given as the examples.

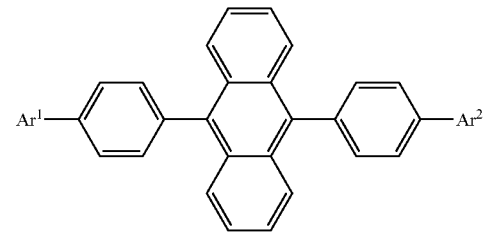

| Compound | $Ar^1$ | $Ar^2$ |
|---|---|---|
| AN-1 | 1-naphthyl | 9-phenanthryl |
| AN-2 | 1-naphthyl | 1-pyrenyl |
| AN-3 | 1-naphthyl | phenyl |
| AN-4 | 1-naphthyl | 2-biphenyl |
| AN-5 | 1-naphthyl | 3-biphenyl |
| AN-6 | 1-naphthyl | 4-biphenyl |
| AN-7 | 1-naphthyl | 2-p-terphenyl |
| AN-8 | 2-naphthyl | 1-naphthyl |
| AN-9 | 2-naphthyl | 9-phenanthryl |
| AN-10 | 2-naphthyl | 1-pyrenyl |
| AN-11 | 2-naphthyl | phenyl |
| AN-12 | 2-naphthyl | 2-biphenyl |
| AN-13 | 2-naphthyl | 3-biphenyl |
| AN-14 | 2-naphthyl | 4-biphenyl |
| AN-15 | 2-naphthyl | 2-p-terphenyl |
| AN-16 | 9-phenanthryl | 1-pyrenyl |
| AN-17 | 9-phenanthryl | phenyl |
| AN-18 | 9-phenanthryl | 2-biphenyl |
| AN-19 | 9-phenanthryl | 3-biphenyl |
| AN-20 | 9-phenanthryl | 4-biphenyl |
| AN-21 | 9-phenanthryl | 2-p-terphenyl |
| AN-22 | 1-pyrenyl | phenyl |
| AN-23 | 1-pyrenyl | 2-biphenyl |
| AN-24 | 1-pyrenyl | 3-biphenyl |
| AN-25 | 1-pyrenyl | 4-biphenyl |
| AN-26 | 1-pyrenyl | 2-p-terphenyl |
| AN-27 | phenyl | 2-biphenyl |
| AN-28 | phenyl | 3-biphenyl |
| AN-29 | phenyl | 4-biphenyl |
| AN-30 | phenyl | 2-p-terphenyl |
| AN-31 | 2-biphenyl | 3-biphenyl |
| AN-32 | 2-biphenyl | 4-biphenyl |
| AN-33 | 2-biphenyl | 2-p-terphenyl |
| AN-34 | 3-biphenyl | 4-biphenyl |
| AN-35 | 3-biphenyl | 2-p-terphenyl |

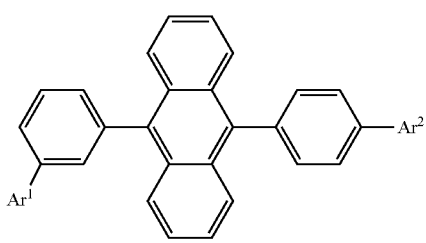

| Compound | Ar¹ | Ar² |
| --- | --- | --- |
| AN-36 | 1-naphthyl | 1-naphthyl |
| AN-37 | 1-naphthyl | 2-naphthyl |
| AN-38 | 1-naphthyl | 9-phenanthryl |
| AN-39 | 1-naphthyl | 1-pyrenyl |
| AN-40 | 1-naphthyl | phenyl |
| AN-41 | 1-naphthyl | 2-biphenyl |
| AN-42 | 1-naphthyl | 3-biphenyl |
| AN-43 | 1-naphthyl | 4-biphenyl |
| AN-44 | 1-naphthyl | 2-p-terphenyl |
| AN-45 | 2-naphthyl | 1-naphthyl |
| AN-46 | 2-naphthyl | 2-naphthyl |
| AN-47 | 2-naphthyl | 9-phenanthryl |
| AN-48 | 2-naphthyl | 1-pyrenyl |
| AN-49 | 2-naphthyl | phenyl |
| AN-50 | 2-naphthyl | 2-biphenyl |
| AN-51 | 2-naphthyl | 3-biphenyl |
| AN-52 | 2-naphthyl | 4-biphenyl |
| AN-53 | 2-naphthyl | 2-p-terphenyl |
| AN-54 | 9-phenanthryl | 1-naphthyl |
| AN-55 | 9-phenanthryl | 2-naphthyl |
| AN-56 | 9-phenanthryl | 9-phenanthryl |
| AN-57 | 9-phenanthryl | 1-pyrenyl |
| AN-58 | 9-phenanthryl | phenyl |
| AN-59 | 9-phenanthryl | 2-biphenyl |
| AN-60 | 9-phenanthryl | 3-biphenyl |
| AN-61 | 9-phenanthryl | 4-biphenyl |
| AN-62 | 9-phenanthryl | 2-p-terphenyl |
| AN-63 | 1-pyrenyl | 1-naphthyl |
| AN-64 | 1-pyrenyl | 2-naphthyl |
| AN-65 | 1-pyrenyl | 9-phenanthryl |
| AN-66 | 1-pyrenyl | 1-pyrenyl |
| AN-67 | 1-pyrenyl | phenyl |
| AN-68 | 1-pyrenyl | 2-biphenyl |
| AN-69 | 1-pyrenyl | 3-biphenyl |
| AN-70 | 1-pyrenyl | 4-biphenyl |
| AN-71 | 1-pyrenyl | 2-p-terphenyl |
| AN-72 | phenyl | 1-naphthyl |
| AN-73 | phenyl | 2-naphthyl |
| AN-74 | phenyl | 9-phenanthryl |
| AN-75 | phenyl | 1-pyrenyl |
| AN-76 | phenyl | phenyl |
| AN-77 | phenyl | 2-biphenyl |
| AN-78 | phenyl | 3-biphenyl |
| AN-79 | phenyl | 4-biphenyl |
| AN-80 | phenyl | 2-p-terphenyl |
| AN-81 | 2-biphenyl | 1-naphthyl |
| AN-82 | 2-biphenyl | 2-naphthyl |
| AN-83 | 2-biphenyl | 9-phenanthryl |
| AN-84 | 2-biphenyl | 1-pyrenyl |
| AN-85 | 2-biphenyl | phenyl |
| AN-86 | 2-biphenyl | 2-biphenyl |
| AN-87 | 2-biphenyl | 3-biphenyl |
| AN-88 | 2-biphenyl | 4-biphenyl |
| AN-89 | 2-biphenyl | 2-p-terphenyl |
| AN-90 | 3-biphenyl | 1-naphthyl |
| AN-91 | 3-biphenyl | 2-naphthyl |
| AN-92 | 3-biphenyl | 9-phenanthryl |
| AN-93 | 3-biphenyl | 1-pyrenyl |
| AN-94 | 3-biphenyl | phenyl |
| AN-95 | 3-biphenyl | 2-biphenyl |
| AN-96 | 3-biphenyl | 3-biphenyl |
| AN-97 | 3-biphenyl | 4-biphenyl |
| AN-98 | 3-biphenyl | 2-p-terphenyl |
| AN-99 | 4-biphenyl | 1-naphthyl |

-continued

| Compound | Ar¹ | Ar² |
| --- | --- | --- |
| AN-100 | 4-biphenyl | 2-naphthyl |
| AN-101 | 4-biphenyl | 9-phenanthryl |
| AN-102 | 4-biphenyl | 1-pyrenyl |
| AN-103 | 4-biphenyl | phenyl |
| AN-104 | 4-biphenyl | 2-biphenyl |
| AN-105 | 4-biphenyl | 3-biphenyl |
| AN-106 | 4-biphenyl | 4-biphenyl |
| AN-107 | 4-biphenyl | 2-p-terphenyl |

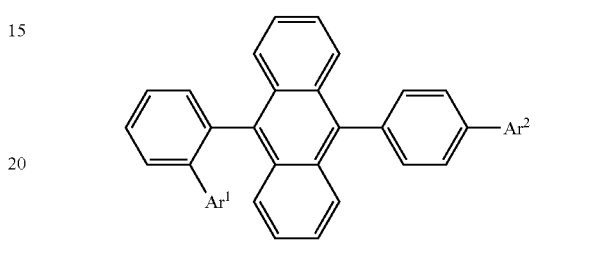

| Compound | Ar¹ | Ar² |
| --- | --- | --- |
| AN-108 | 1-naphthyl | 1-naphthyl |
| AN-109 | 1-naphthyl | 2-naphthyl |
| AN-110 | 1-naphthyl | 9-phenanthryl |
| AN-111 | 1-naphthyl | 1-pyrenyl |
| AN-112 | 1-naphthyl | phenyl |
| AN-113 | 1-naphthyl | 2-biphenyl |
| AN-114 | 1-naphthyl | 3-biphenyl |
| AN-115 | 1-naphthyl | 4-biphenyl |
| AN-116 | 1-naphthyl | 2-p-terphenyl |
| AN-117 | 2-naphthyl | 1-naphthyl |
| AN-118 | 2-naphthyl | 2-naphthyl |
| AN-119 | 2-naphthyl | 9-phenanthryl |
| AN-120 | 2-naphthyl | 1-pyrenyl |
| AN-121 | 2-naphthyl | phenyl |
| AN-122 | 2-naphthyl | 2-biphenyl |
| AN-123 | 2-naphthyl | 3-biphenyl |
| AN-124 | 2-naphthyl | 4-biphenyl |
| AN-125 | 2-naphthyl | 2-p-terphenyl |
| AN-126 | 9-phenanthryl | 1-naphthyl |
| AN-127 | 9-phenanthryl | 2-naphthyl |
| AN-128 | 9-phenanthryl | 9-phenanthryl |
| AN-129 | 9-phenanthryl | 1-pyrenyl |
| AN-130 | 9-phenanthryl | phenyl |
| AN-131 | 9-phenanthryl | 2-biphenyl |
| AN-132 | 9-phenanthryl | 3-biphenyl |
| AN-133 | 9-phenanthryl | 4-biphenyl |
| AN-134 | 9-phenanthryl | 2-p-terphenyl |
| AN-135 | 1-pyrenyl | 1-naphthyl |
| AN-136 | 1-pyrenyl | 2-naphthyl |
| AN-137 | 1-pyrenyl | 9-phenanthryl |
| AN-138 | 1-pyrenyl | 1-pyrenyl |
| AN-139 | 1-pyrenyl | phenyl |
| AN-140 | 1-pyrenyl | 2-biphenyl |
| AN-141 | 1-pyrenyl | 3-biphenyl |
| AN-142 | 1-pyrenyl | 4-biphenyl |
| AN-143 | 1-pyrenyl | 2-p-terphenyl |
| AN-144 | phenyl | 1-naphthyl |
| AN-145 | phenyl | 2-naphthyl |
| AN-146 | phenyl | 9-phenanthryl |
| AN-147 | phenyl | 1-pyrenyl |
| AN-148 | phenyl | phenyl |
| AN-149 | phenyl | 2-biphenyl |
| AN-150 | phenyl | 3-biphenyl |
| AN-151 | phenyl | 4-biphenyl |
| AN-152 | phenyl | 2-p-terphenyl |
| AN-153 | 2-biphenyl | 1-naphthyl |
| AN-154 | 2-biphenyl | 2-naphthyl |
| AN-155 | 2-biphenyl | 9-phenanthryl |

-continued

| Compound | Ar¹ | Ar² |
|---|---|---|
| AN-156 | 2-biphenyl | 1-pyrenyl |
| AN-157 | 2-biphenyl | phenyl |
| AN-158 | 2-biphenyl | 2-biphenyl |
| AN-159 | 2-biphenyl | 3-biphenyl |
| AN-160 | 2-biphenyl | 4-biphenyl |
| AN-161 | 2-biphenyl | 2-p-terphenyl |
| AN-162 | 3-biphenyl | 1-naphthyl |
| AN-163 | 3-biphenyl | 2-naphthyl |
| AN-164 | 3-biphenyl | 9-phenanthryl |
| AN-165 | 3-biphenyl | 1-pyrenyl |
| AN-166 | 3-biphenyl | phenyl |
| AN-167 | 3-biphenyl | 2-biphenyl |
| AN-168 | 3-biphenyl | 3-biphenyl |
| AN-169 | 3-biphenyl | 4-biphenyl |
| AN-170 | 3-biphenyl | 2-p-terphenyl |
| AN-171 | 4-biphenyl | 1-naphthyl |
| AN-172 | 4-biphenyl | 2-naphthyl |
| AN-173 | 4-biphenyl | 9-phenanthryl |
| AN-174 | 4-biphenyl | 1-pyrenyl |
| AN-175 | 4-biphenyl | phenyl |
| AN-176 | 4-biphenyl | 2-biphenyl |
| AN-177 | 4-biphenyl | 3-biphenyl |
| AN-178 | 4-biphenyl | 4-biphenyl |
| AN-179 | 4-biphenyl | 2-p-terphenyl |

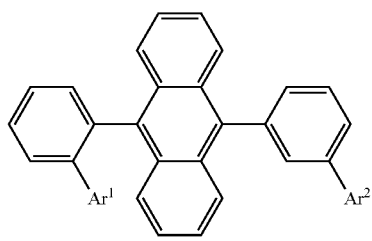

| Compound | Ar¹ | Ar² |
|---|---|---|
| AN-180 | 1-naphthyl | 1-naphthyl |
| AN-181 | 1-naphthyl | 2-naphthyl |
| AN-182 | 1-naphthyl | 9-phenanthryl |
| AN-183 | 1-naphthyl | 1-pyrenyl |
| AN-184 | 1-naphthyl | phenyl |
| AN-185 | 1-naphthyl | 2-biphenyl |
| AN-186 | 1-naphthyl | 3-biphenyl |
| AN-187 | 1-naphthyl | 4-biphenyl |
| AN-188 | 2-naphthyl | 1-naphthyl |
| AN-189 | 2-naphthyl | 2-naphthyl |
| AN-190 | 2-naphthyl | 9-phenanthryl |
| AN-191 | 2-naphthyl | 1-pyrenyl |
| AN-192 | 2-naphthyl | phenyl |
| AN-193 | 2-naphthyl | 2-biphenyl |
| AN-194 | 2-naphthyl | 3-biphenyl |
| AN-195 | 2-naphthyl | 4-biphenyl |
| AN-196 | 9-phenanthryl | 1-naphthyl |
| AN-197 | 9-phenanthryl | 2-naphthyl |
| AN-198 | 9-phenanthryl | 9-phenanthryl |
| AN-199 | 9-phenanthryl | 1-pyrenyl |
| AN-200 | 9-phenanthryl | phenyl |
| AN-201 | 9-phenanthryl | 2-biphenyl |
| AN-202 | 9-phenanthryl | 3-biphenyl |
| AN-203 | 9-phenanthryl | 4-biphenyl |
| AN-204 | 1-pyrenyl | 1-naphthyl |
| AN-205 | 1-pyrenyl | 2-naphthyl |
| AN-206 | 1-pyrenyl | 9-phenanthryl |
| AN-207 | 1-pyrenyl | 1-pyrenyl |
| AN-208 | 1-pyrenyl | phenyl |
| AN-209 | 1-pyrenyl | 2-biphenyl |
| AN-210 | 1-pyrenyl | 3-biphenyl |
| AN-211 | 1-pyrenyl | 4-biphenyl |

| Compound | Ar¹ | Ar² |
|---|---|---|
| AN-212 | phenyl | 1-naphthyl |
| AN-213 | phenyl | 2-naphthyl |
| AN-214 | phenyl | 9-phenanthryl |
| AN-215 | phenyl | 1-pyrenyl |
| AN-216 | phenyl | phenyl |
| AN-217 | phenyl | 2-biphenyl |
| AN-218 | phenyl | 3-biphenyl |
| AN-219 | phenyl | 4-biphenyl |
| AN-220 | 2-biphenyl | 1-naphthyl |
| AN-221 | 2-biphenyl | 2-naphthyl |
| AN-222 | 2-biphenyl | 9-phenanthryl |
| AN-223 | 2-biphenyl | 1-pyrenyl |
| AN-224 | 2-biphenyl | phenyl |
| AN-225 | 2-biphenyl | 2-biphenyl |
| AN-226 | 2-biphenyl | 3-biphenyl |
| AN-227 | 2-biphenyl | 4-biphenyl |
| AN-228 | 3-biphenyl | 1-naphthyl |
| AN-229 | 3-biphenyl | 2-naphthyl |
| AN-230 | 3-biphenyl | 9-phenanthryl |
| AN-231 | 3-biphenyl | 1-pyrenyl |
| AN-232 | 3-biphenyl | phenyl |
| AN-233 | 3-biphenyl | 2-biphenyl |
| AN-234 | 3-biphenyl | 3-biphenyl |
| AN-235 | 3-biphenyl | 4-biphenyl |
| AN-236 | 4-biphenyl | 1-naphthyl |
| AN-237 | 4-biphenyl | 2-naphthyl |
| AN-238 | 4-biphenyl | 9-phenanthryl |
| AN-239 | 4-biphenyl | 1-pyrenyl |
| AN-240 | 4-biphenyl | phenyl |
| AN-241 | 4-biphenyl | 2-biphenyl |
| AN-242 | 4-biphenyl | 3-biphenyl |
| AN-243 | 4-biphenyl | 4-biphenyl |

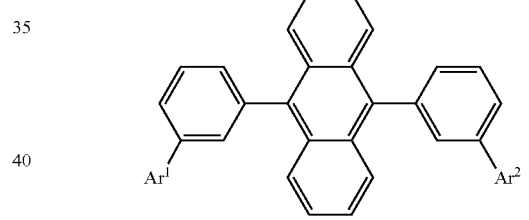

| Compound | Ar¹ | Ar² |
|---|---|---|
| AN-244 | 1-naphthyl | 2-naphthyl |
| AN-245 | 1-naphthyl | 9-phenanthryl |
| AN-246 | 1-naphthyl | 1-pyrenyl |
| AN-247 | 1-naphthyl | phenyl |
| AN-248 | 1-naphthyl | 2-biphenyl |
| AN-249 | 1-naphthyl | 3-biphenyl |
| AN-250 | 1-naphthyl | 4-biphenyl |
| AN-251 | 2-naphthyl | 9-phenanthryl |
| AN-252 | 2-naphthyl | 1-pyrenyl |
| AN-253 | 2-naphthyl | phenyl |
| AN-254 | 2-naphthyl | 2-biphenyl |
| AN-255 | 2-naphthyl | 3-biphenyl |
| AN-256 | 2-naphthyl | 4-biphenyl |
| AN-257 | 9-phenanthryl | 1-pyrenyl |
| AN-258 | 9-phenanthryl | phenyl |
| AN-259 | 9-phenanthryl | 2-biphenyl |
| AN-260 | 9-phenanthryl | 3-biphenyl |
| AN-261 | 9-phenanthryl | 4-biphenyl |
| AN-262 | 1-pyrenyl | phenyl |
| AN-263 | 1-pyrenyl | 2-biphenyl |
| AN-264 | 1-pyrenyl | 3-biphenyl |
| AN-265 | 1-pyrenyl | 4-biphenyl |
| AN-266 | phenyl | 2-biphenyl |
| AN-267 | phenyl | 3-biphenyl |

-continued

| Compound | Ar¹ | Ar² |
|---|---|---|
| AN-268 | phenyl | 4-biphenyl |
| AN-269 | 2-biphenyl | 3-biphenyl |
| AN-270 | 2-biphenyl | 4-biphenyl |
| AN-271 | 3-biphenyl | 4-biphenyl |

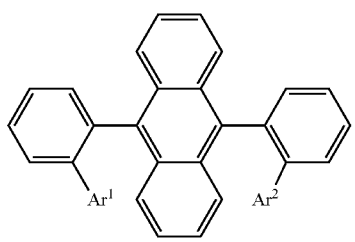

| Compound | Ar¹ | Ar² |
|---|---|---|
| AN-272 | 1-naphthyl | 2-naphthyl |
| AN-273 | 1-naphthyl | 9-phenanthryl |
| AN-274 | 1-naphthyl | 1-pyrenyl |
| AN-275 | 1-naphthyl | phenyl |
| AN-276 | 1-naphthyl | 2-biphenyl |
| AN-277 | 1-naphthyl | 3-biphenyl |
| AN-278 | 1-naphthyl | 4-biphenyl |
| AN-279 | 2-naphthyl | 9-phenanthryl |
| AN-280 | 2-naphthyl | 1-pyrenyl |
| AN-281 | 2-naphthyl | phenyl |
| AN-282 | 2-naphthyl | 2-biphenyl |
| AN-283 | 2-naphthyl | 3-biphenyl |
| AN-284 | 2-naphthyl | 4-biphenyl |
| AN-285 | 9-phenanthryl | 1-pyrenyl |
| AN-286 | 9-phenanthryl | phenyl |
| AN-287 | 9-phenanthryl | 2-biphenyl |
| AN-288 | 9-phenanthryl | 3-biphenyl |
| AN-289 | 9-phenanthryl | 4-biphenyl |
| AN-290 | 1-pyrenyl | phenyl |
| AN-291 | 1-pyrenyl | 2-biphenyl |
| AN-292 | 1-pyrenyl | 3-biphenyl |
| AN-293 | 1-pyrenyl | 4-biphenyl |
| AN-294 | phenyl | 2-biphenyl |
| AN-295 | phenyl | 3-biphenyl |
| AN-296 | phenyl | 4-biphenyl |
| AN-297 | 2-biphenyl | 3-biphenyl |
| AN-298 | 2-biphenyl | 4-biphenyl |
| AN-299 | 3-biphenyl | 4-biphenyl |

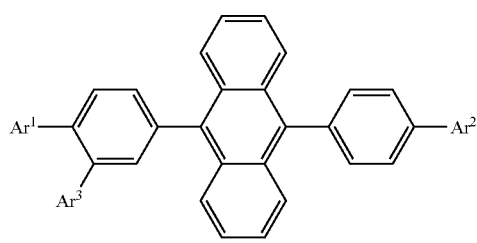

| Compound | Ar¹ | Ar² |
|---|---|---|
| AN-300 | 1-naphthyl | 1-naphthyl |
| AN-301 | 1-naphthyl | 2-naphthyl |
| AN-302 | 1-naphthyl | 9-phenanthryl |

| Compound | Ar¹ | Ar² |
|---|---|---|
| AN-303 | 1-naphthyl | 1-pyrenyl |
| AN-304 | 1-naphthyl | phenyl |
| AN-305 | 1-naphthyl | 2-biphenyl |
| AN-306 | 1-naphthyl | 3-biphenyl |
| AN-307 | 1-naphthyl | 4-biphenyl |
| AN-308 | 1-naphthyl | 2-p-terphenyl |
| AN-309 | 2-naphthyl | 1-naphthyl |
| AN-310 | 2-naphthyl | 2-naphthyl |
| AN-311 | 2-naphthyl | 9-phenanthryl |
| AN-312 | 2-naphthyl | 1-pyrenyl |
| AN-313 | 2-naphthyl | phenyl |
| AN-314 | 2-naphthyl | 2-biphenyl |
| AN-315 | 2-naphthyl | 3-biphenyl |
| AN-316 | 2-naphthyl | 4-biphenyl |
| AN-317 | 2-naphthyl | 2-p-terphenyl |

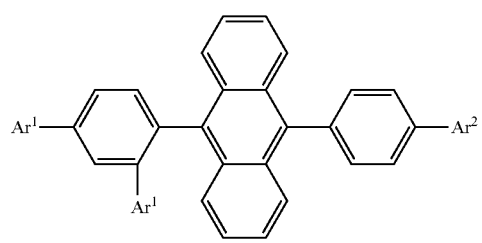

| Compound | Ar¹ | Ar² |
|---|---|---|
| AN-318 | 1-naphthyl | 1-naphthyl |
| AN-319 | 1-naphthyl | 2-naphthyl |
| AN-320 | 1-naphthyl | 9-phenanthryl |
| AN-321 | 1-naphthyl | 1-pyrenyl |
| AN-322 | 1-naphthyl | phenyl |
| AN-323 | 1-naphthyl | 2-biphenyl |
| AN-324 | 1-naphthyl | 3-biphenyl |
| AN-325 | 1-naphthyl | 4-biphenyl |
| AN-326 | 1-naphthyl | 2-p-terphenyl |
| AN-327 | 2-naphthyl | 1-naphthyl |
| AN-328 | 2-naphthyl | 2-naphthyl |
| AN-329 | 2-naphthyl | 9-phenanthryl |
| AN-330 | 2-naphthyl | 1-pyrenyl |
| AN-331 | 2-naphthyl | phenyl |
| AN-332 | 2-naphthyl | 2-biphenyl |
| AN-333 | 2-naphthyl | 3-biphenyl |
| AN-334 | 2-naphthyl | 4-biphenyl |
| AN-335 | 2-naphthyl | 2-p-terphenyl |

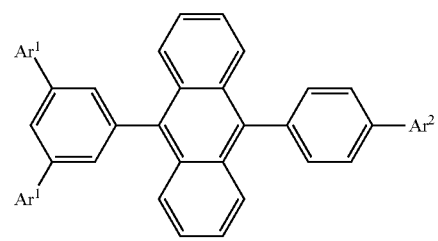

| Compound | Ar¹ | Ar² |
|---|---|---|
| AN-336 | 1-naphthyl | 1-naphthyl |
| AN-337 | 1-naphthyl | 2-naphthyl |

| Compound | Ar¹ | Ar² |
|---|---|---|
| AN-338 | 1-naphthyl | 9-phenanthryl |
| AN-339 | 1-naphthyl | 1-pyrenyl |
| AN-340 | 1-naphthyl | phenyl |
| AN-341 | 1-naphthyl | 2-biphenyl |
| AN-342 | 1-naphthyl | 3-biphenyl |
| AN-343 | 1-naphthyl | 4-biphenyl |
| AN-344 | 1-naphthyl | 2-p-terphenyl |
| AN-345 | 2-naphthyl | 1-naphthyl |
| AN-346 | 2-naphthyl | 2-naphthyl |
| AN-347 | 2-naphthyl | 9-phenanthryl |
| AN-348 | 2-naphthyl | 1-pyrenyl |
| AN-349 | 2-naphthyl | phenyl |
| AN-350 | 2-naphthyl | 2-biphenyl |
| AN-351 | 2-naphthyl | 3-biphenyl |
| AN-352 | 2-naphthyl | 4-biphenyl |
| AN-353 | 2-naphthyl | 2-p-terphenyl |

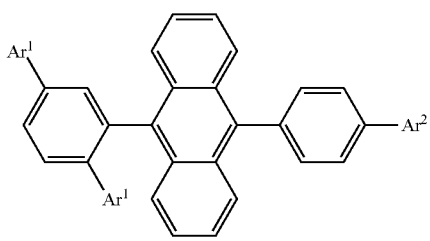

| Compound | Ar¹ | Ar² |
|---|---|---|
| AN-354 | 1-naphthyl | 1-naphthyl |
| AN-355 | 1-naphthyl | 2-naphthyl |
| AN-356 | 1-naphthyl | 9-phenanthryl |
| AN-357 | 1-naphthyl | 1-pyrenyl |
| AN-358 | 1-naphthyl | phenyl |
| AN-359 | 1-naphthyl | 2-biphenyl |
| AN-360 | 1-naphthyl | 3-biphenyl |
| AN-361 | 1-naphthyl | 4-biphenyl |
| AN-362 | 1-naphthyl | 2-p-terphenyl |
| AN-363 | 2-naphthyl | 1-naphthyl |
| AN-364 | 2-naphthyl | 2-naphthyl |
| AN-365 | 2-naphthyl | 9-phenanthryl |
| AN-366 | 2-naphthyl | 1-pyrenyl |
| AN-367 | 2-naphthyl | phenyl |
| AN-368 | 2-naphthyl | 2-biphenyl |
| AN-369 | 2-naphthyl | 3-biphenyl |
| AN-370 | 2-naphthyl | 4-biphenyl |
| AN-371 | 2-naphthyl | 2-p-terphenyl |

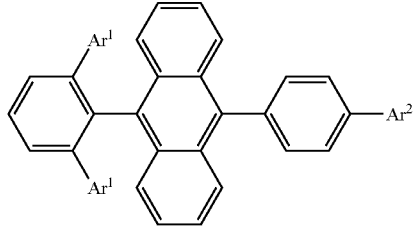

| Compound | Ar¹ | Ar² |
|---|---|---|
| AN-372 | 1-naphthyl | 1-naphthyl |
| AN-373 | 1-naphthyl | 2-naphthyl |
| AN-374 | 1-naphthyl | 9-phenanthryl |
| AN-375 | 1-naphthyl | 1-pyrenyl |
| AN-376 | 1-naphthyl | phenyl |
| AN-377 | 1-naphthyl | 2-biphenyl |
| AN-378 | 1-naphthyl | 3-biphenyl |
| AN-379 | 1-naphthyl | 4-biphenyl |
| AN-380 | 1-naphthyl | 2-p-terphenyl |
| AN-381 | 2-naphthyl | 1-naphthyl |
| AN-382 | 2-naphthyl | 2-naphthyl |
| AN-383 | 2-naphthyl | 9-phenanthryl |
| AN-384 | 2-naphthyl | 1-pyrenyl |
| AN-385 | 2-naphthyl | phenyl |
| AN-386 | 2-naphthyl | 2-biphenyl |
| AN-387 | 2-naphthyl | 3-biphenyl |
| AN-388 | 2-naphthyl | 4-biphenyl |
| AN-389 | 2-naphthyl | 2-p-terphenyl |

AN-390

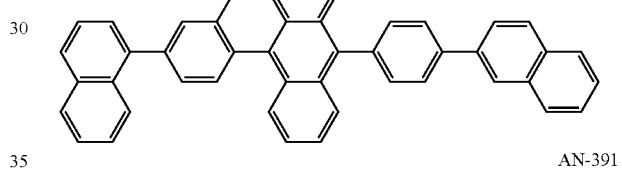

AN-391

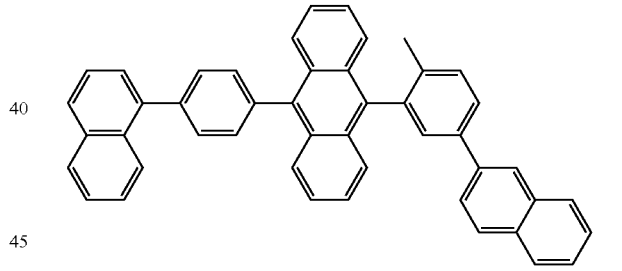

AN-392

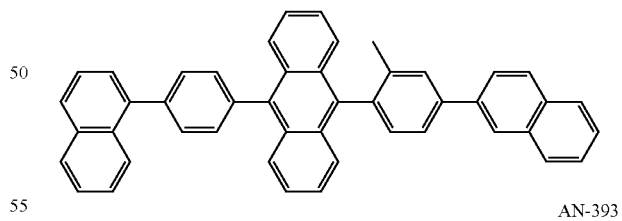

AN-393

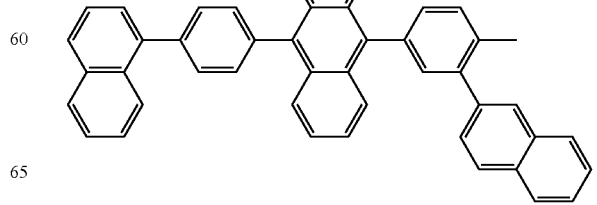

AN-394
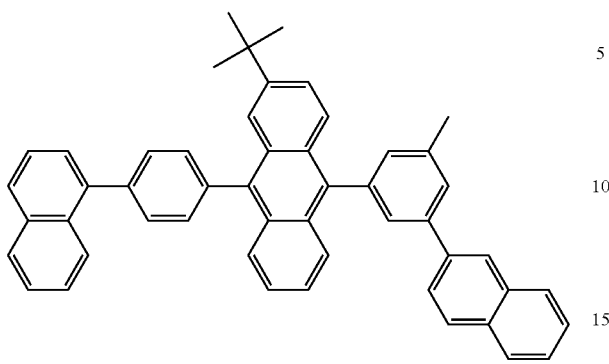
AN-395
AN-396
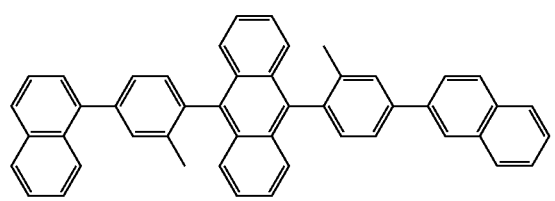
AN-397
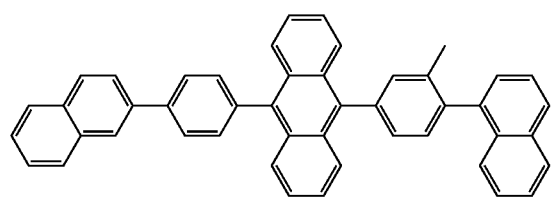
AN-398
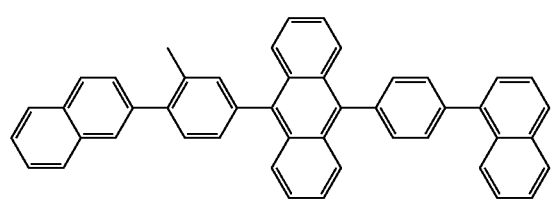
AN-399
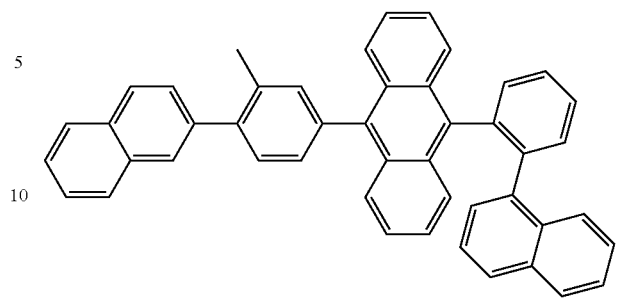
AN-400
AN-401
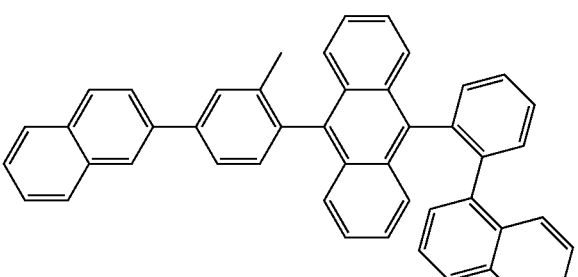
AN-402

-continued
AN-403
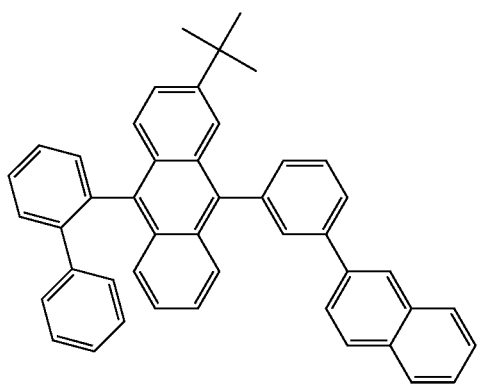
AN-404
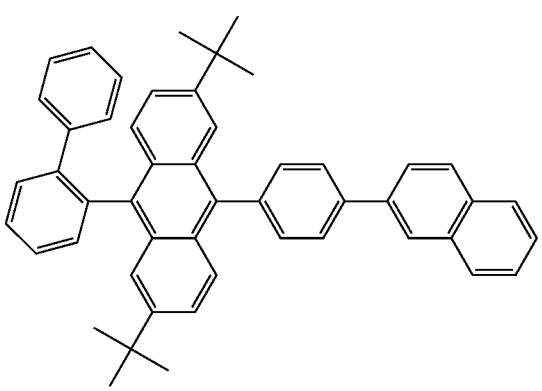
AN-405
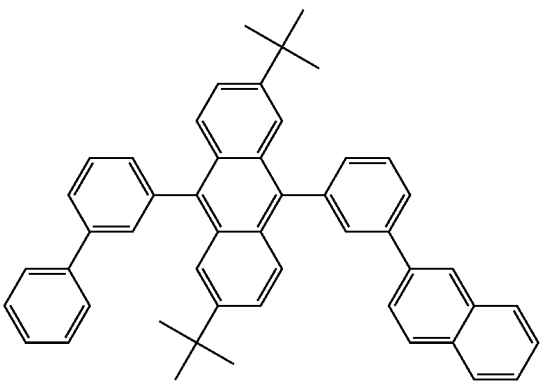
AN-406
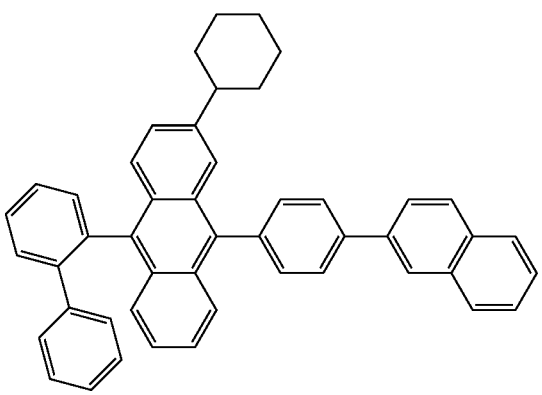
-continued
AN-407
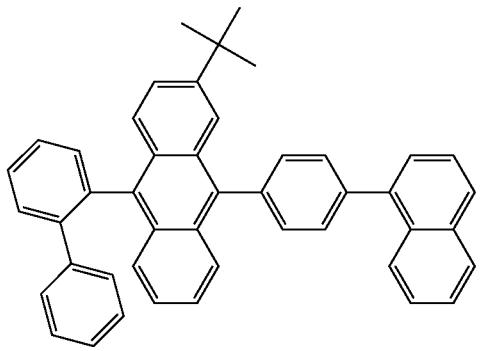
AN-408
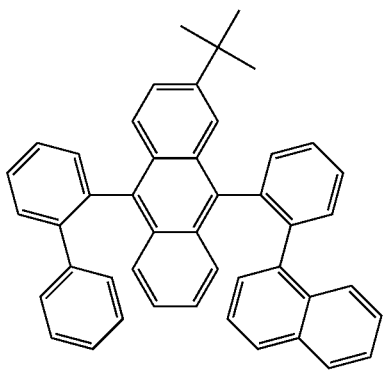
AN-409
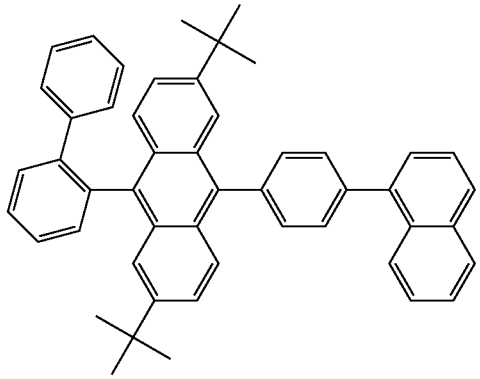
AN-410
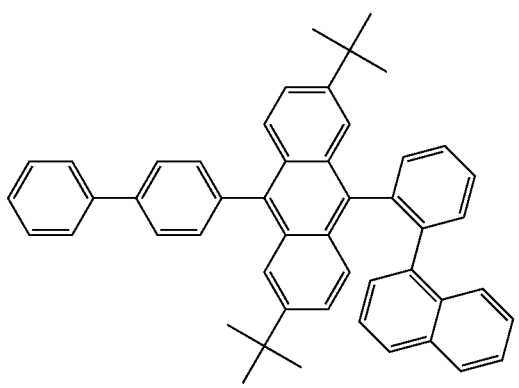

-continued
AN-411
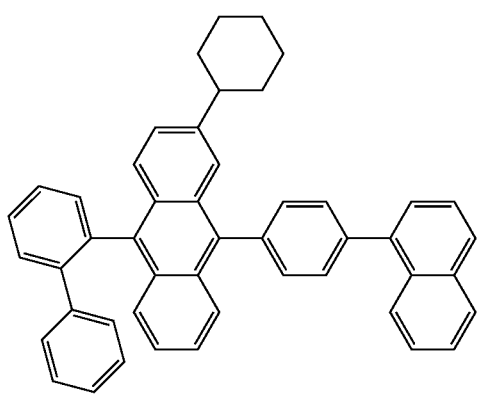
AN-415
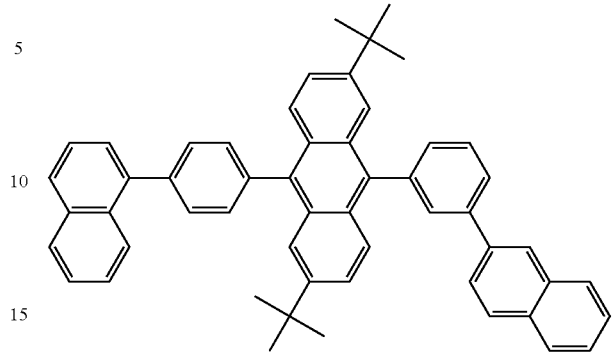
AN-412
AN-416
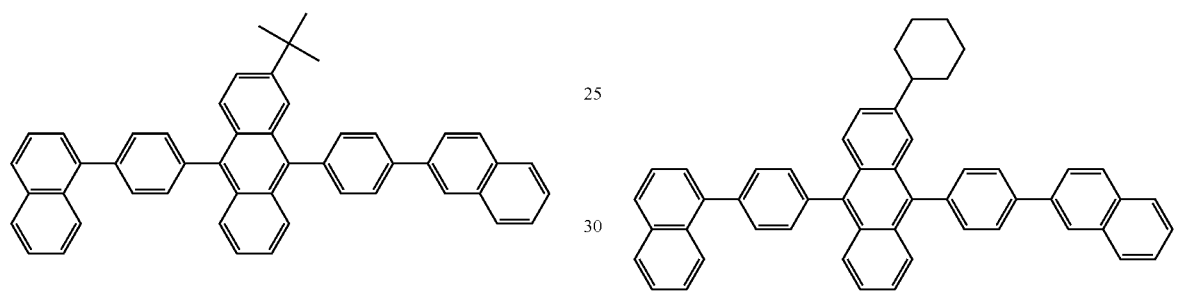
AN-413
AN-417
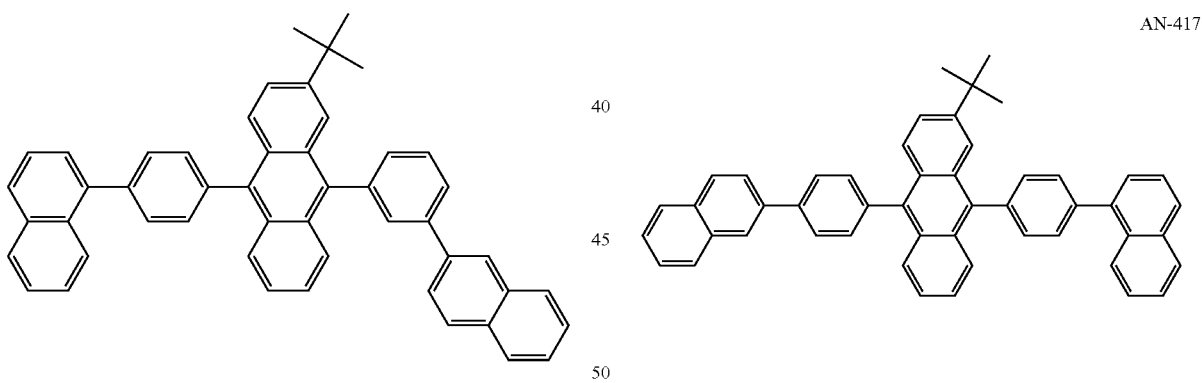
AN-414
AN-418
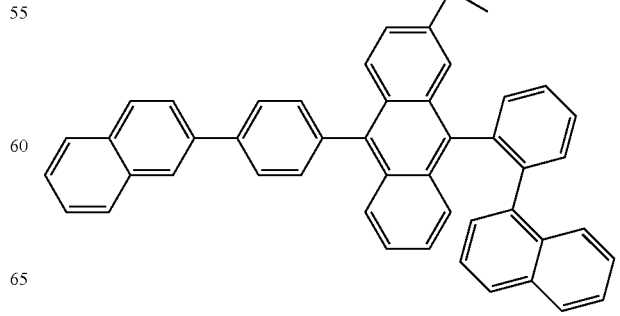

AN-419

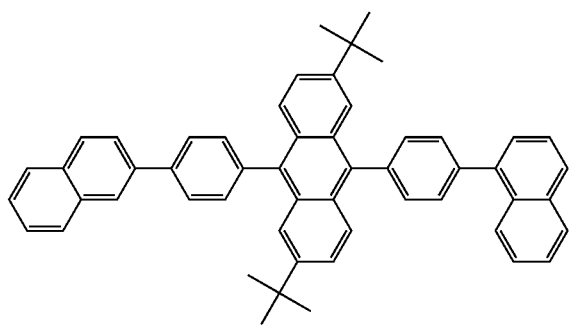

AN-420

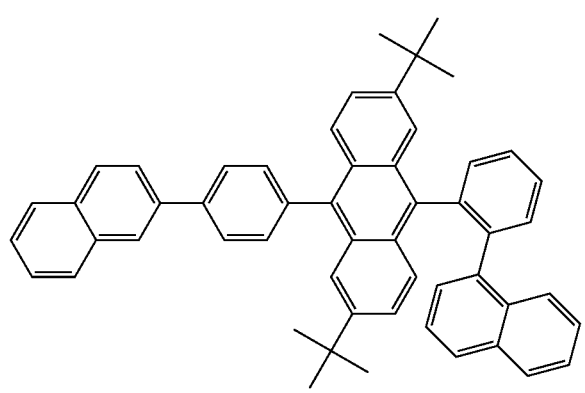

AN-421

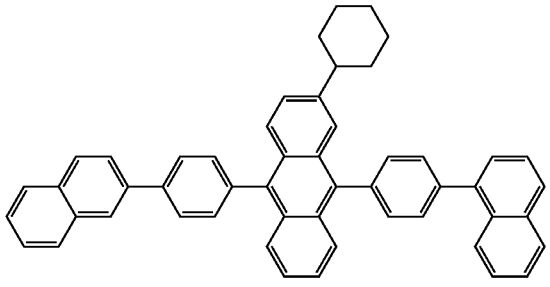

The asymmetric monoanthracene derivative of the present invention represented by Formula (1) can be synthesized by suitably combining Suzuki coupling reaction, halogenation reaction and boration reaction which are publicly known methods using halogenated aryl derivatives and anthrylboronic acid derivative as starting materials. The synthetic scheme thereof shall be shown below.

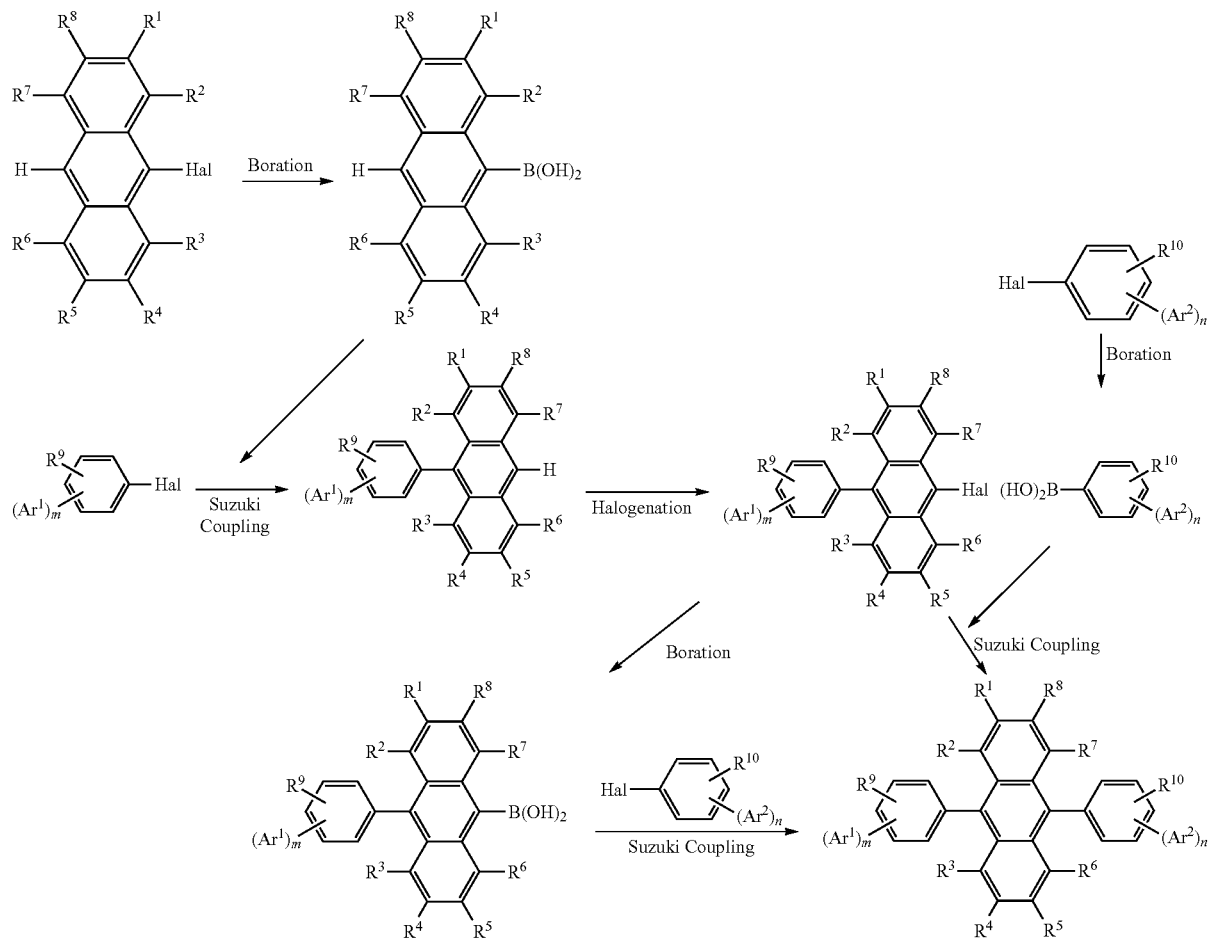

A lot of reports (Chem. Rev., Vol. 95, No. 7, 2457 (1995) and the like) has so far been made on the Suzuki coupling reaction, and it can be carried out on reaction conditions described in these reports.

Usually, the reaction is carried out at atmospheric pressure under inert atmosphere of nitrogen, argon and helium, and it can be carried out as well, if necessary, under a pressurized condition. The reaction temperature falls in a range of 15 to 300° C., particularly preferably 30 to 200° C.

Capable of being used as the reaction solvent alone or in a mixture are water, aromatic hydrocarbons such as benzene, toluene and xylene, ethers such as 1,2-dimethoxyethane, diethyl ether, methyl t-butyl ether, tetrahydrofuran and dioxane, saturated hydrocarbons such as pentane, hexane, heptane, octane and cyclohexane, halides such as dichloromethane, chloroform, carbon tetrachloride, 1,2-dichloroethane and 1,1,1-trichloroethane, nitriles such as acetonitrile and benzonitrile, esters such as ethyl acetate, methyl acetate and butyl acetate and amides such as N,N-dimethylformamide, N,N-dimethylacetamide and N-methylpyrrolidone. Among them, toluene, 1,2-dimethoxyethane, dioxane and water are preferred. A use amount of the solvent is usually 3 to 50 weight times, preferably 4 to 20 weight times based on arylboronic acid or a derivative thereof.

The base used for the reaction includes, for example, sodium carbonate, potassium carbonate, sodium hydroxide, potassium hydroxide, sodium hydrogencarbonate, potassium hydrogencarbonate, magnesium carbonate, lithium carbonate, potassium fluoride, cesium fluoride, cesium chloride, cesium bromide, cesium carbonate, potassium phosphate, sodium methoxide, potassium t-butoxide, sodium t-butoxide and lithium t-butoxide, and it is preferably sodium carbonate. A use amount of the above bases is usually 0.7 to 10 mole equivalent, preferably 0.9 to 6 mole equivalent based on arylboronic acid or a derivative thereof.

The catalyst used for the reaction includes, for example, palladium catalysts such as tetrakis(triphenylphosphine)palladium, dichlorobis(triphenylphosphine)palladium, dichloro[bis(diphenylphosphino)ethane]palladium, dichloro[bis(diphenylphosphino)propane]palladium, dichloro[bis(diphenylphosphino)butane]palladium and dichloro[bis(diphenylphosphino)ferrocene]palladium and nickel catalysts such as tetrakis(triphenylphosphine)nickel, dichlorobis(triphenylphosphine)nickel, dichloro[bis(diphenylphosphino)ethane]nickel, dichloro[bis(diphenylphosphino)propane]nickel, dichloro[bis(diphenylphosphino)butane]nickel and dichloro[bis(diphenylphosphino)ferrocene]nickel, and it is preferably tetrakis(triphenylphosphine) palladium. A use amount of the above catalysts is usually 0.001 to 1 mole equivalent, preferably 0.01 to 0.1 mole equivalent based on the halogenated anthracene derivative.

Halogen of the halogenated anthracene derivative includes, for example, an iodine atom, a bromine atom and a chlorine atom, and it is preferably an iodine atom and a bromine atom.

A halogenating agent in the halogenation reaction shall not specifically be restricted, and N-halogenated succinimide is suitably used. A use amount of the halogenating agent is usually 0.8 to 10 mole equivalent, preferably 1 to 5 mole equivalent based on the anthracene derivative.

Usually, the reaction is carried out in an inert solvent under an inert atmosphere of nitrogen, argon and helium. The inert solvent includes, for example, N,N-dimethylformamide, N,N-dimethylacetamide, N-methylpyrrolidone, dimethyl sulfoxide, carbon tetrachloride, chlorobenzene, dichlorobenzene, nitrobenzene, toluene, xylene, methyl cellosolve, ethyl cellosolve and water, and it is preferably N,N-dimethylformamide and N-methylpyrrolidone. A use amount of the solvent is usually 3 to 50 weight times, preferably 5 to 20 weight times based on the anthracene derivative. The reaction is carried out at a temperature of usually 0 to 200° C., preferably 20 to 120° C.

The boration reaction can be carried out by known methods (Experimental Chemistry Course Fourth Edition, vol. 24, p. 61 to 90, edited by Japan Chemical Society, J. Org. Chem., Vol. 70, 7508 (1995) and the like). In the case of, for example, the reaction via lithiation of halogenated anthracene derivatives or Grignard reaction, it is carried out usually under an inert atmosphere of nitrogen, argon and helium, and an inert solvent is used as the reaction solvent. Capable of being used as the reaction solvent alone or in a mixture are, for example, saturated hydrocarbons such as pentane, hexane, heptane, octane and cyclohexane, ethers such as 1,2-dimethoxyethane, diethyl ether, methyl t-butyl ether, tetrahydrofuran and dioxane and aromatic hydrocarbons such as benzene, toluene and xylene, and it is preferably diethyl ether and toluene. A use amount of the solvent is usually 3 to 50 weight times, preferably 4 to 20 weight times based on the halogenated anthracene derivative.

Capable of being used as the lithiation agent are, for example, alkyl metal reagents such as n-butyllithium, t-butyllithium, phenyllithium and methyllithium and amide bases such as lithium diisopropylamide and lithium bistrimethylsilylamide, and it is preferably n-butyllithium. The Grignard reagent can be prepared by reacting the halogenated anthracene derivative with metallic magnesium. Capable of being used as trialkyl borate which is the boration agent are, for example, trimethyl borate, triethyl borate, triisopropyl borate and tributyl borate, and it is preferably trimethyl borate and triisopropyl borate.

The use amounts of the lithiation agent and metallic magnesium each are usually 1 to 10 mole equivalent, preferably 1 to 2 mole equivalent based on the halogenated anthracene derivative. A use amount of trialkyl borate is usually 1 to 10 mole equivalent, preferably 1 to 5 mole equivalent based on the halogenated anthracene derivative. The reaction temperature is usually −100 to 50° C., preferably −75 to 10° C.

The organic EL device of the present invention is an organic EL device in which an organic thin film layer comprising a single layer or plural layers including a luminescent layer is interposed between a cathode and an anode, wherein at least one of the above thin film layers contains the asymmetric monoanthracene derivative represented by Formula (1) described above in the form of a single component or a mixed component.

In the organic EL device of the present invention, the luminescent layer described above preferably contains the asymmetric monoanthracene derivative represented by Formula (1) as a principal component.

Further, in the organic EL device of the present invention, the luminescent layer described above preferably further contains an arylamine compound and/or a styrylamine compound.

The styrylamine compound is preferably a compound represented by the following Formula (A):

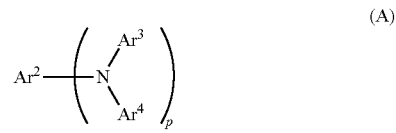

(A)

(wherein $Ar^2$ is a group selected from a phenyl group, a biphenyl group, a terphenyl group, a stilbene group and a distyrylaryl group; $Ar^3$ and $Ar^4$ each are a hydrogen atom or an aromatic hydrocarbon ring group having 6 to 20 carbon atoms, and $Ar^2$, $Ar^3$ and $Ar^4$ may be substituted; p is an integer of 1 to 4; and more preferably, at least one of $Ar^3$ and $Ar^4$ is substituted with a styryl group).

In this regard, the aromatic hydrocarbon ring group having 6 to 20 carbon atoms includes phenyl, naphthyl, anthranyl, phenanthryl and terphenyl.

The arylamine compound is preferably a compound represented by the following Formula (B):

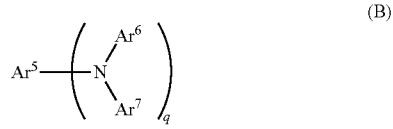

(wherein $Ar^5$ to $Ar^7$ are a substituted or non-substituted aryl group having 5 to 40 nuclear carbon atoms; and q is an integer of 1 to 4).

In this regard, the aryl group having 5 to 40 nuclear carbon atoms includes, for example, phenyl, naphthyl, anthranyl, phenanthryl, pyrenyl, coronyl, biphenyl, terphenyl, pyrrolyl, furanyl, thiophenyl, benzothiophenyl, oxadiazolyl, diphenylanthranyl, indolyl, carbazolyl, pyridyl, benzoquinolyl, fluoroanthenyl, acenaphthofluoranthenyl, stilbene, perylenyl, chrysenyl, picenyl, triphenylenyl, rubicenyl, benzoanthracenyl, phenylanthranyl, bisanthracenyl and aryl groups represented by the following Formulas (C) and (D):

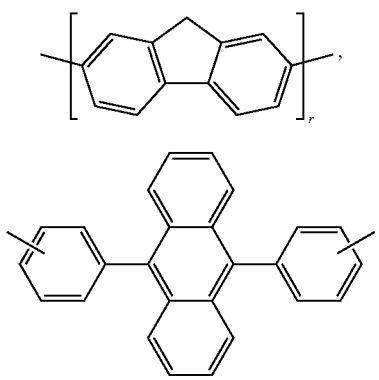

(in Formula (C), r is an integer of 1 to 3).

Preferred substituents of the aryl group described above include an alkyl group having 1 to 6 carbon atoms (ethyl, methyl, i-propyl, n-propyl, s-butyl, t-butyl, pentyl, hexyl, cyclopentyl and cyclohexyl), an alkoxy group having 1 to 6 carbon atoms (ethoxy, methoxy, i-propoxy, n-propoxy, s-butoxy, t-butoxy, pentoxy, hexyloxy, cyclopentoxy and cyclohexyloxy), an aryl group having 5 to 40 nuclear carbon atoms, an amino group substituted with an aryl group having 5 to 40 nuclear carbon atoms, an ester group having an aryl group having 5 to 40 nuclear carbon atoms, an ester group having an alkyl group having 1 to 6 carbon atoms, a cyano group, a nitro group and a halogen atom.

$Ar^5$ is particularly preferably naphthyl, anthranyl, chrysenyl, pyrenyl or the aryl group represented by Formula (D), which are substituted or non-substituted respectively.

The material for the organic EL device of the present invention comprises the asymmetric monoanthracene derivative represented by Formula (1) described above, and it is preferably a luminescent material. Further, it is preferably a host material.

The device structure of the organic EL device of the present invention shall be explained below.

The typical examples of the device structure of the organic EL device of the present invention include structure such as:

(1) anode/luminescent layer/cathode,
(2) anode/hole injecting layer/luminescent layer/cathode,
(3) anode/luminescent layer/electron injecting layer/cathode,
(4) anode/hole injecting layer/luminescent layer/electron injecting layer/cathode,
(5) anode/organic semiconductor layer/luminescent layer/cathode,
(6) anode/organic semiconductor layer/electron barrier layer/luminescent layer/cathode,
(7) anode/organic semiconductor layer/luminescent layer/adhesion improving layer/cathode,
(8) anode/hole injecting layer/hole transporting layer/luminescent layer/electron injecting layer/cathode
(9) anode/insulating layer/luminescent layer/insulating layer/cathode,
(10) anode/inorganic semiconductor layer/insulating layer/luminescent layer/insulating layer/cathode
(11) anode/organic semiconductor layer/insulating, layer/luminescent layer/insulating layer/cathode,
(12) anode/insulating layer/hole injecting layer/hole transporting layer/luminescent layer/insulating layer/cathode and
(13) anode/insulating layer/hole injecting layer/hole transporting layer/luminescent layer/electron injecting layer/cathode Among them, usually the structure of (8) is preferably used, but it shall not be restricted to them.

The above organic EL device is usually prepared on a light transmitting substrate. This light transmitting substrate is a substrate supporting the organic EL device, and as far as a light transmitting property thereof is concerned, a substrate in which light in a visible region of 400 to 700 nm has a transmission factor of 50% or more is preferred, and a flat substrate is preferably used.

For example, a glass plate and a synthetic resin plate are preferably used as the above light transmitting substrate. The glass plate includes plates molded particularly by soda lime glass, barium.strontium-containing glass, lead glass, alumi-nosilicate glass, borosilicate glass, barium borosilicate glass and quartz. The synthetic resin plate includes plates of polycarbonate resins, acryl resins, polyethylene terephthalate resins, polyether sulfide resins and polysulfone resins.

Next, the anode assumes a role to inject a hole into the hole transporting layer or the luminescent layer, and it is effective to provide the anode with a work function of 4.5 eV or more. The specific examples of a material for the anode used in the present invention include indium tin oxide alloy (ITO), tin oxide (NESA), gold, silver, platinum and copper. The cathode is preferably a material having a small work function for the purpose of injecting an electron into the electron transporting layer or the luminescent layer.

The anode can be prepared by forming a thin film of the above electrode substances by a method such as a deposition method and a sputtering method.

When light emitted from the luminescent layer is taken out from the anode, a transmission factor of the anode based on light emitted is preferably larger than 10%. A sheet resistance of the anode is preferably several hundred Ω/□ or less. A film thickness of the anode is selected, though depending on the material, in a range of usually 10 nm to 1 μm, preferably 10 to 200 nm.

In the organic EL device of the present invention, the luminescent layer has:

(1) an injecting function: a function in which a hole can be injected from an anode or a hole injecting layer in applying an electric field and in which an electron can be injected from a cathode or an electron injecting layer,
(2) a transporting function: a function in which a charge injected (electron and hole) is migrated by virtue of a force of an electric field and
(3) a luminescent function: a function in which a field for recombination of an electron and a hole is provided and in which this is connected to luminescence.

A publicly known method such as, for example, a deposition method, a spin coating method and an LB method can be applied as a method for forming the above luminescent layer. In particular, the luminescent layer is preferably a molecular deposit film. In this case, the molecular deposit film means a thin film formed by depositing a material compound staying in a gas phase state and a film formed by solidifying a material compound staying in a solution state or a liquid phase state, and usually the above molecular deposit film can be distinguished from a thin film (molecular accumulation film) formed by the LB method by a difference in an aggregation structure and a higher order structure and a functional difference originating in it.

Further, as disclosed in Japanese Patent Application Laid-Open No. 51781/1982, the luminescent layer can be formed as well by dissolving a binding agent such as a resin and the material compound in a solvent to prepare a solution and then coating the solution by a spin coating method to form a thin film.

Other publicly known luminescent materials other than the luminescent material of the present invention may be added, if necessary, to the luminescent layer as long as the object of the present invention is not damaged. Further, a luminescent layer containing a different publicly known luminescent material may be laminated on the luminescent layer containing the luminescent material of the present invention.

Next, the hole injecting and transporting layers are layers for assisting injection of a hole into the luminescent layer to transport it to the luminescent region, and they have a large hole mobility and have a small ionization energy of usually 5.5 eV or less. A material which transports a hole to the luminescent layer by a lower electric field strength is preferred as the above hole injecting and transporting layers, and more preferred is a material in which a mobility of a hole is at least $10^{-6}$ cm$^2$/V·second in applying an electric field of, for example, $10^4$ to $10^6$ V/cm. Capable of being used as the above material are optional materials selected from materials which have so far conventionally been used as charge transporting materials of holes in photoconductive materials and publicly known materials which are used for a hole injecting layer in an organic EL device.

The specific examples thereof include, for example, triazole derivatives (refer to U.S. Pat. No. 3,112,197), oxadiazole derivatives (refer to U.S. Pat. No. 3,189,447), imidazole derivatives (refer to Japanese Patent Publication No. 16096/1962), polyarylalkane derivatives (refer to U.S. Pat. No. 3,615,402, ditto U.S. Pat. No. 3,820,989 and ditto U.S. Pat. No. 3,542,544, Japanese Patent Publication No. 555/1970 and ditto 10983/1976 and Japanese Patent Application Laid-Open No. 93224/1976, ditto 17105/1980, ditto 4148/1981, ditto 10866/1980, ditto 156953/1980 and ditto 36656/1981), pyrazoline derivatives and pyrazolone derivatives (refer to U.S. Pat. No. 3,180,729 and ditto U.S. Pat. No. 4,278,746 and Japanese Patent Application Laid-Open No. 88064/1980, ditto 88065/1980, ditto 105537/1974, ditto 51086/1980, ditto 80051/1981, ditto 88141/1981, ditto 45545/1982, ditto 112637/1979 and ditto 74546/1980), phenylenediamine derivatives (refer to U.S. Pat. No. 3,615,404, Japanese Patent Publication No. 10105/1976, ditto 3712/1971 and ditto 25336/1972 and Japanese Patent Application Laid-Open No. 53435/1979, ditto 110536/1979 and ditto 119925/1979), arylamine derivatives (refer to U.S. Pat. No. 3,567,450, ditto U.S. Pat. No. 3,180,703, ditto U.S. Pat. No. 3,240,597, ditto U.S. Pat. No. 3,658,520, ditto U.S. Pat. No. 4,232,103, ditto U.S. Pat. No. 4,175,961 and ditto U.S. Pat. No. 4,012,376, Japanese Patent Publication No. 35702/1974 and ditto 27577/1964, Japanese Patent Application Laid-Open No. 144250/1980, ditto 119132/1981 and ditto 22437/1981 and German Patent 1,110,518), amino-substituted chalcone derivatives (refer to U.S. Pat. No. 3,526,501), oxazole derivatives (disclosed in U.S. Pat. No. 3,257,203), styrylanthracene derivatives (refer to Japanese Patent Application Laid-Open No. 46234/1981), fluorenone derivatives (refer to Japanese Patent Application Laid-Open No. 110837/1979), hydrazone derivatives (refer to U.S. Pat. No. 3,717,462, Japanese Patent Application Laid-Open No. 59143/1979, ditto 52063/1980, ditto 52064/1980, ditto 46760/1980, ditto 85495/1980, ditto 11350/1982 and ditto 148749/1982 and Japanese Patent Application Laid-Open No. 311591/1990), stilbene derivatives (Japanese Patent Application Laid-Open No. 210363/1986, ditto 228451/1986, ditto 14642/1986, ditto 72255/1986, ditto 47646/1987, ditto 36674/1987, ditto 10652/1987, ditto 30255/1987, ditto 93455/1985, ditto 94462/1985, ditto 174749/1985 and ditto 175052/1985), silazane derivatives (refer to U.S. Pat. No. 4,950,950), polysilane base (refer to Japanese Patent Application Laid-Open No. 204996/1990), aniline base copolymers (refer to Japanese Patent Application Laid-Open No. 282263/1990) and electroconductive high molecular oligomers (particularly thiophene oligomers) disclosed in Japanese Patent Application Laid-Open No. 211399/1989.

The compounds described above can be used as the material for the hole injecting layer, and preferably used are porphyrin compounds (disclosed in Japanese Patent Application Laid-Open No. 2956965/1988), aromatic tertiary amine compounds and styrylamine compounds (refer to U.S. Pat. No. 4,127,412 and Japanese Patent Application Laid-Open No. 27033/1978, ditto 58445/1979, ditto 149634/1979, ditto 64299/1979, ditto 79450/1980, ditto 144250/1980, ditto 119132/1981, ditto 295558/1986, ditto 98353/1986 and ditto 295695/1988), and the aromatic tertiary amine compounds are particularly preferably used.

Further, capable of being given are compounds having two condensed aromatic rings in a molecule described in U.S. Pat. No. 5,061,569, for example, 4,4'-bis(N-(1-naphthyl)-N-phenylamino)biphenyl (hereinafter abbreviated as NPD) and 4,4',4"-tris(N-(3-methylphenyl)-N-phenylamino)triphenyl (hereinafter abbreviated as MTDATA) in which three triphenylamine units are combined in the form of a star burst type disclosed in Japanese Patent Application Laid-Open No. 308688/1992.

Further, inorganic compounds such as p type Si, p type SiC and the like in addition to the aromatic dimethylidene base compounds described above shown as the material for the luminescent layer can also be used as the material for the hole injecting layer.

The hole injecting and transporting layers can be formed by making a thin film from the compound described above by a publicly known method such as, for example, a vacuum deposition method, a spin coating method, a casting method and an LB method. A film thickness of the hole injecting and transporting layers shall not specifically be restricted, and it is usually 5 nm to 5 μm. The above hole injecting and transporting layers may be constituted from a single layer comprising at least one of the materials described above as long as the compound of the present invention is contained in the hole transporting zone, and hole injecting and transporting layers comprising compounds which are different from those used in the hole injecting and transporting layers described above may be laminated thereon.

Further, an organic semiconductor layer is a layer for assisting injection of a hole or injection of an electron into the luminescent layer, and the layer having an electric conductivity of $10^{-10}$ S/cm or more is suited. Capable being used as a material for the above organic semiconductor layer are conductive oligomers such as thiophene-containing oligomers and arylamine-containing oligomers disclosed in Japanese Patent Application Laid-Open No. 193191/1996 and conductive dendrimers such as arylamine-containing dendrimers.

Next, the electron injecting and transporting layers are layers for assisting injection of an electron into the luminescent layer to transport it to the luminescent region, and they have a large electron mobility. Also, the adhesion improving layer is a layer comprising particularly a material having a good adhesive property with the cathode in the above electron injecting layer. The metal complexes of 8-hydroxyquinoline or the derivatives thereof and oxadiazole derivatives are suited as a material used for the electron injecting layer. The specific examples of the above metal complexes of 8-hydroxyquinoline or the derivatives thereof include metal chelate oxynoid compounds containing chelates of oxine (in general, 8-quinolinol or 8-hydroxyquinoline), and, for example, tris(8-quinolinol)aluminum can be used as the electron injecting material.

On the other hand, the oxadiazole derivative includes electron transmitting compounds represented by the following formulas:

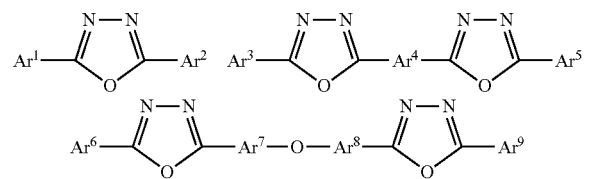

wherein $Ar^{1'}$, $Ar^{2'}$, $Ar^{3'}$, $Ar^{5'}$, $Ar^{6'}$ and $Ar^{9'}$ each represent a substituted or non-substituted aryl group, and they may be the same as or different from each other; $Ar^{4'}$, $Ar^{7'}$ and $Ar^{8'}$ each represent a substituted or non-substituted arylene group, and they may be the same as or different from each other.

In this connection, the aryl group includes phenyl, biphenyl, anthranyl, perylenyl and pyrenyl. Also, the arylene group includes phenylene, naphthylene, biphenylene, anthranylene, perylenylene and pyrenylene. The substituents therefor include an alkyl group having 1 to 10 carbon atoms, an alkoxy group having 1 to 10 carbon atoms and a cyano group. The above electron transmitting compounds have preferably a thin film-forming property.

The following compounds can be given as the specific examples of the electron transmitting compounds described above:

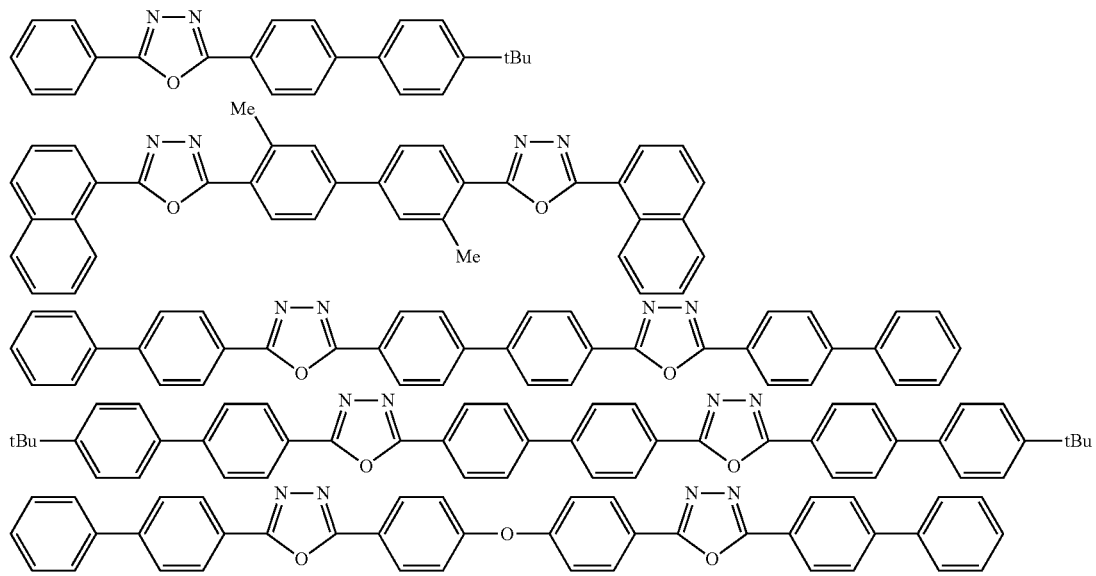

The preferred mode of the organic EL device of the present invention includes a device containing a reducing dopant in the region which transports an electron or an interfacial region between the cathode and the organic layer. In this case, the reducing dopant is defined by a substance which can reduce an electron transporting compound. Accordingly, various compounds can be used as long as they have a reducing property of some extent, and capable of being suitably used is at least one substance selected from the group consisting of, for example, alkaline metals, alkaline earth metals, rare earth metals, oxides of alkaline metals, halides of alkaline metals, oxides of alkaline earth metals, halides of alkaline earth metals, oxides of rare earth metals or halides of rare earth metals, organic complexes of alkaline metals, organic complexes of alkaline earth metals and organic complexes of rare earth metals.

To be more specific, the preferred reducing dopant includes at least one alkaline metal selected from the group consisting of Na (work function: 2.36 eV), K (work function: 2.28 eV), Rb (work function: 2.16 eV) and Cs (work function: 1.95 eV) and at least one alkaline earth metal selected from the group consisting of Ca (work function: 2.9 eV), Sr (work function: 2.0 to 2.5 eV) and Ba (work function: 2.52 eV), and the compounds having a work function of 2.9 eV or less are particularly preferred. Among them, the more preferred reducing dopant is at least one alkaline metal selected from the group consisting of K, Rb and Cs, and it is more preferably Rb or Cs. It is most preferably Cs. The above alkaline metals have a particularly high reducing ability, and addition of a relatively small amount thereof to the electron injecting zone makes it possible to raise a light emitting luminance and extend the life thereof in the organic EL device. The combination of two or more kinds of the above alkaline metals is preferred as the reducing dopant having a work function of 2.9 eV or less, and particularly preferred is the combination containing Cs, for example, Cs and Na, Cs and K, Cs and Rb or Cs, Na and K. Containing Cs in combination makes it possible to efficiently exhibit the reducing ability, and addition thereof to the electron injecting zone makes it possible to raise a light emitting luminance and extend the life thereof in the organic EL element.

In the present invention, an electron injecting layer constituted from an insulator and a semiconductor may further be provided between the cathode and the organic layer. In this case, an electric current can effectively be prevented from leaking to raise the electron injecting property. Preferably used as the above insulator is at least one metal compound selected from the group consisting of alkaline metal chalcogenides, alkaline earth metal chalcogenides, halides of alkaline metals and halides of alkaline earth metals. If the electron injecting layer is constituted from the above alkaline metal chalcogenides, it is preferred from the viewpoint that the electron injecting property can further be enhanced. To be specific, the preferred alkaline metal chalcogenides include, for example, $Li_2O$, LiO, $Na_2S$, $Na_2Se$ and NaO, and the preferred alkaline earth metal chalcogenides include, for example, CaO, BaO, SrO, BeO, BaS and CaSe. Also, the preferred halides of alkaline metals include, for example, LiF, NaF, KF, LiCl, KCl and NaCl. Further, the preferred halides of alkaline earth metals include, for example, fluorides such as $CaF_2$, $BaF_2$, $SrF_2$, $MgF_2$ and $BeF_2$ and halides other than the fluorides.

The semiconductor constituting the electron transporting layer includes one kind alone of oxides, nitrides or nitride oxides containing at least one element of Ba, Ca, Sr, Yb, Al, Ga, In, Li, Na, Cd, Mg, Si, Ta, Sb and Zn or combinations of two or more kinds thereof. The inorganic compound constituting the electron transporting layer is preferably a crystallite or amorphous insulating thin film. If the electron transporting layer is constituted from the above insulating thin film, the more homogeneous thin film is formed, and therefore picture element defects such as dark spots can be reduced. The above inorganic compound includes the alkaline metal chalcogenides, the alkaline earth metal chalcogenides, the halides of alkaline metals and the halides of alkaline earth metals each described above.

Next, electrodes using metals, alloys, electroconductive compounds and mixtures thereof each having a small work function (4 eV or less) for the electrode material are used as the cathode. The specific examples of the above electrode material include sodium, sodium-potassium alloys, magnesium, lithium, magnesium silver alloys, aluminum/aluminum oxide, $Al/Li_2O$, $Al/LiO_2$, Al/LiF, aluminum.lithium alloys, indium and rare earth metals.

The above cathode can be prepared by forming a thin film from the above electrode materials by a method such as deposition and sputtering.

In this respect, when light emitted from the luminescent layer is taken out from the cathode, a transmission factor of the cathode based on light emitted is preferably larger than 10%. A sheet resistance of the cathode is preferably several hundred $\Omega/\square$ or less, and a film thickness thereof is usually 10 nm to 1 μm, preferably 50 to 200 nm.

In general, in an organic EL device, an electric field is applied to a ultrathin film, and therefore it is liable to cause picture element defects by leak and short. In order to prevent this, an insulating thin film layer may be interposed between a pair of the electrodes.

A material used for the insulating layer includes, for example, aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide and vanadium oxide, and mixtures and laminates thereof may be used.

Next, in respect to a process for preparing the organic EL device of the present invention, the anode, the luminescent layer, if necessary, the hole injecting layer and, if necessary, the electron injecting layer are formed according to the materials and the methods each described above, and finally the cathode is formed. Also, the organic EL device can be prepared as well from the cathode to the anode in an order which is reverse to what was described above.

A preparation example of the organic EL device having a structure in which an anode/a hole injecting layer/a luminescent layer/an electron injecting layer/a cathode are provided in order on a light transmitting substrate shall be explained below.

First, a thin film comprising an anode material is formed on a suitable light transmitting substrate by a deposition method or a sputtering method so that a film thickness falls in a range of 1 μm or less, preferably 10 to 200 nm, whereby an anode is prepared. Next, a hole injecting layer is provided on the above anode. The hole injecting layer can be formed, as described above, by a method such as a vacuum deposition method, a spin coating method, a casting method and an LB method, and it is preferably formed by the vacuum deposition method from the viewpoints that the homogeneous film is liable to be obtained and that pinholes are less liable to be produced. When forming the hole injecting layer by the vacuum deposition method, the depositing conditions thereof are varied according to the compounds used (a material for the hole injecting layer), the crystal structure of the intended hole injecting layer and the recombination structure, and in general, they are suitably selected preferably in the ranges of a depositing source temperature of 50 to 450° C., a vacuum degree of $10^{-7}$ to $10^{-3}$ torr, a depositing speed of 0.01 to 50 nm/second, a substrate temperature of −50 to 300° C. and a film thickness of 5 nm to 5 μm.

Next, a luminescent layer is provided on the above hole injecting layer. This luminescent layer can be formed by making a thin film from the luminescent material according to the present invention by a method such as a vacuum deposition method, a sputtering method, a spin coating method and a casting method, and it is preferably formed by the vacuum deposition method from the viewpoints that the homogeneous film is liable to be obtained and that pinholes are less liable to be produced. When forming the luminescent layer by the vacuum deposition method, the depositing conditions thereof are varied according to the compounds used, and in general, they can be selected from the same condition ranges as in forming the hole injecting layer. The layer thickness falls preferably in a range of 10 to 40 nm.

Next, an electron injecting layer is provided on the above luminescent layer. Also in this case, it is preferably formed by the vacuum deposition method as is the case with the hole injecting layer and the luminescent layer since the homogeneous film has to be obtained. The depositing conditions thereof can be selected from the same condition ranges as in the hole injecting layer and the luminescent layer.

Lastly, a cathode is laminated, whereby an organic EL device can be obtained. The cathode is constituted from metal, and therefore the deposition method and the sputtering method can be used. However, the vacuum deposition method is preferred in order to protect the organic substance layer of the base from being damaged in making the film.

The above organic EL device is preferably prepared serially from the anode up to the cathode in one vacuuming.

The forming methods of the respective layers in the organic EL device of the present invention shall not specifically be restricted, and the forming methods carried out by the vacuum deposition method and the spin coating method which have so far publicly been known can be used. The organic thin film containing the compound represented by Formula (1) described above which is used for the organic EL device of the present invention can be formed by a publicly known method carried out by a coating method such as a vacuum deposition method, a molecular beam evaporation method (MBE method), a dipping method using a solution prepared by dissolving the compound in a solvent, a spin coating method, a casting method, a bar coating method and a roll coating method.

The film thicknesses of the respective organic layers in the organic EL device of the present invention shall not specifically be restricted, and it falls preferably in a range of usually several nm to 1 μm in order to prevent defects such as pinholes and improve the efficiency.

When applying a direct voltage to the organic EL device, luminance can be observed by applying a voltage of 5 to 40 V setting a polarity of the anode to plus and that of the cathode to minus. An electric current does not flow by applying a voltage with the reverse polarities, and luminance is not caused at all. Further, when applying an AC voltage, uniform luminance can be observed only when the anode has a polarity of plus and the cathode has a polarity of minus. The waveform of an alternating current applied may be optional.

EXAMPLES

Next, the present invention shall be explained in further details with reference to examples, but the present invention shall by no means be restricted by these examples.

Synthetic Example 1

Synthesis of 2-(4-bromophenyl)naphthalene

4-Bromoiodobenzene 25.0 g, 2-naphthaleneboronic acid 12.7 g and tetrakis(triphenylphosphine)palladium 1.7 g were mixed and substituted with argon. Toluene 220 ml and a 2M sodium carbonate aqueous solution 110 ml were added thereto, and the mixture was heated and refluxed for 7 hours.

After left cooling, the organic layer was extracted with toluene, and the extract was washed with water and saturated brine. The organic layer was dried on anhydrous sodium sulfate, and then the solvent was distilled off. The crystallized product was filtered and dried, whereby targeted 2-(4-bromophenyl)naphthalene 17.7 g (yield: 85%) was obtained in the form of white crystal.

Synthetic Example 2

Synthesis of 9-anthraceneboronic acid

9-Bromoanthracene 38.6 g was dissolved in dehydrated toluene 80 ml and dehydrated THF (tetrahydrofuran) 160 ml, and the solution was cooled to −40° C. A 1.58M n-butyllithium hexane solution 106 ml was dropwise added thereto and stirred at −40° C. for 30 minutes, the temperature was elevated up to −10° C. The solution was cooled again down to −70° C., and a dehydrated THF solution of trimethyl borate 50.0 ml was gradually dropwise added thereto. The solution was stirred at −70° C. for 2 hours and then slowly heated up to room temperature. After left standing for a night, a 10% hydrochloric acid aqueous solution 100 ml was added thereto and stirred, and then it was extracted twice with toluene. The organic layer was washed with saturated brine and dried on anhydrous sodium sulfate. The solvent was distilled off, and the residue was crystallized from toluene/hexane, filtered and dried, whereby targeted 9-anthraceneboronic acid 24.4 g was obtained in the form of pale brown crystal (yield: 73%).

Synthetic Example 3

Synthesis of 9-(4-naphthalene-2-yl-phenyl)anthracene

9-Anthraceneboronic acid 10.7 g, 2-(4-bromophenyl) naphthalene 11.3 g and tetrakis(triphenylphosphine)palladium 2.3 g were mixed and substituted with argon. DME (dimethoxyethane) 140 ml and a 2M sodium carbonate aqueous solution 60 ml were added thereto, and the mixture was heated and refluxed for 5 hours.

After left cooling, the deposited crystal was filtered and washed with ethanol and toluene. The crystal thus obtained was recrystallized from toluene, filtered and dried, whereby targeted (9-(4-naphthalene-2-yl-phenyl)anthracene 13.25 g was obtained (yield: 87%).

Synthetic Example 4

Synthesis of 9-bromo-10-(4-naphthalene-2-yl-phenyl)anthracene 9-(4-Naphthalene-2-yl-phenyl)anthracene 13.25 g was dispersed in DMF (dimethylformamide) 100 ml, and a DMF solution (100 ml) of NBS (N-bromosuccinimide) 7.44 g was dropwise added thereto at room temperature. The solution was stirred at room temperature for 7 hours and then left standing for a nigh. Water 200 ml was added thereto, and the deposited crystal was filtered, sufficiently washed with ethanol and dried, whereby targeted (9-bromo-10-(4-naphthalene-2-yl-phenyl)anthracene 15.84 g was obtained (yield: 99%).

Synthetic Example 5

Synthesis of 10-(4-naphthalene-2-yl-phenyl)anthracene-9-boronic acid

9-Bromo-10-(4-naphthalene-2-yl-phenyl)anthracene 13.8 g was dispersed in dehydrated toluene 80 ml and dehydrated ether 80 ml, and the mixture was cooled down to −30° C. A 1.58M n-butyllithium hexane solution 21. 0 ml was dropwise added thereto, and after the solution was stirred at −40°

C. for 30 minutes, the temperature was elevated up to −10° C. The solution was cooled again down to −70° C., and a dehydrated ether solution of trimethyl borate 10.0 ml was gradually added thereto. The solution was stirred at −70° C. for 2 hours and then gradually heated up to room temperature. After left standing for a night, a 10% hydrochloric acid aqueous solution 100 ml was added thereto and stirred, and then it was extracted twice with toluene. The organic layer was washed with saturated brine and dried on anhydrous sodium sulfate. The solvent was distilled off, and the residue was crystallized from toluene/hexane, filtered and dried, whereby targeted 10-(4-naphthalene-2-yl-phenyl)anthracene-9-boronic acid 8.48 g was obtained in the form of yellow crystal (yield: 67%).

Synthetic Example 6

Synthesis of 1-(4-bromophenyl)naphthalene 1-(4-Bromophenyl)naphthalene was synthesized by the same method, except that in Synthetic Example 1, 1-naphthaleneboronic acid was used in place of 2-naphthaleneboronic acid.

Synthetic Example 7

Synthesis of 9-phenanthreneboronic acid

9-Phenanthreneboronic acid was synthesized by the same method, except that in Synthetic Example 2, 9-bromophenanthrene was used in place of 9-bromoanthracene.

Synthetic Example 8

Synthesis of 9-(4-bromophenyl)phenanthrene 9-(4-Bromophenyl)phenanthrene was synthesized by the same method, except that in Synthetic Example 1, 9-phenanthreneboronic acid was used in place of 2-naphthaleneboronic acid.

Synthetic Example 9

Synthesis of 10-(biphenyl-2-yl)anthracene-9-boronic acid 10-(Biphenyl-2-yl)anthracene-9-boronic acid was synthesized by the same method, except that in Synthetic Example 3, 2-bromobiphenyl was used as a starting material in place of 2-(4-bromophenyl)naphthalene.

Synthetic Example 10

Synthesis of 9-(4-bromophenyl)-10-phenylanthracene

10-Bromoanthracene-9-boronic acid was synthesized by the same method, except that in Synthetic Example 3, bromobenzene was used as a starting material in place of 2-(4-bromophenyl)naphthalene. Further, it was turned into 4-bromophenyl by the same method as in Synthetic Example 1 to synthesize 9-(4-bromophenyl)-10-phenylanthracene.

Synthetic Example 11

Synthesis of 10-(4-naphthalene-1-yl-phenyl)anthracene-9-boronic acid 10-(4-Naphthalene-1-yl-phenyl)anthracene-9-boronic acid was synthesized by the same method, except that in Synthetic Example 1, 1-naphthaleneboronic acid was used as a starting material in place of 2-naphthaleneboronic acid.

Synthetic Example 12

Synthesis of 2-(3-bromophenyl)naphthalene 2-(3-Bromophenyl)naphthalene was synthesized by the same method, except that in Synthetic Example 1, 3-bromoiodobenzene was used in place of 4-bromoiodobenzene.

Synthetic Example 13

Synthesis of 2-(2-bromophenyl)naphthalene 2-(2-Bromophenyl)naphthalene was synthesized by the same method, except that in Synthetic Example 1, 2-bromoiodobenzene was used in place of 4-bromoiodobenzene.

Synthetic Example 14

Synthesis of 10-(p-terphenyl-2-yl)anthracene-9-boronic acid 10-(p-Terphenyl-2-yl)anthracene-9-boronic acid was synthesized by the same method, except that in Synthetic Example 3, 2-bromo-p-terphenyl was used as a starting material in place of 2-(4-bromophenyl)naphthalene.

Synthetic Example 15

Synthesis of 1-(3-bromophenyl)naphthalene 1-(3-Bromophenyl)naphthalene was synthesized by the same method, except that in Synthetic Example 1, 3-bromoiodobenzene was used in place of 4-bromoiodobenzene and that 1-naphthaleneboronic acid was used in place of 2-naphthaleneboronic acid.

Synthetic Example 16

Synthesis of 9-(biphenyl-2-yl)-10-(3-bromophenyl)anthracene 10-(2-Biphenyl)anthracene-9-boronic acid was synthesized by the same method, except that in Synthetic Example 3, 2-bromobiphenyl was used in place of 2-(4-bromophenyl)naphthalene. Further, it was turned into 3-bromophenyl by the same method as in Synthetic Example 1 to synthesize 9-(biphenyl-2-yl)-10-(3-bromophenyl)anthracene.

Synthetic Example 17

Synthesis of 10-(3-naphthalene-2-yl-phenyl)anthracene-9-boronic acid 10-(3-Naphthalene-2-yl-phenyl)anthracene-9-boronic acid was synthesized by the same method, except that in Synthetic Example 1, 3-bromoiodobenzene was used as a starting material in place of 4-bromoiodobenzene.

Synthetic Example 18

Synthesis of 9-(3-bromophenyl)phenanthrene 9-(3-Bromophenyl)phenanthrene was synthesized by the same method, except that in Synthetic Example 1, 9-phenanthreneboronic acid was used in place of 2-naphthaleneboronic acid and that 3-bromoiodobenzene was used in place of 4-bromoiodobenzene.

Synthetic Example 19

Synthesis of 1-(2-bromophenyl)naphthalene 1-(3-Bromophenyl)naphthalene was synthesized by the same method, except that in Synthetic Example 1, 2-bromoiodobenzene was used in place of 4-bromoiodobenzene and that 1-naphthaleneboronic acid was used in place of 2-naphthaleneboronic acid.

Synthetic Example 20

Synthesis of 2-(3-bromo-5-naphthalene-2-yl-phenyl)naphthalene 1,3,5-Tribromoiodobenzene 10 g, 2-naphthaleneboronic acid 12 g and tetrakis(triphenylphosphine)palladium 1.1 g were mixed and substituted with argon. Toluene 150 ml and a 2M sodium carbonate aqueous solution 55 ml were added thereto, and the mixture was heated and refluxed for 7 hours. After left cooling, the organic layer was extracted with toluene, and the extract was washed with water and saturated brine. The organic layer was dried on anhydrous sodium sulfate, and then the solvent was distilled off. The product was refined by silica gel chromatography, whereby targeted 2-(3-bromo-5-naphthalene-2-yl-phenyl)naphthalene 5.5 g (yield: 42%) was obtained in the form of white crystal.

Synthetic Example 21

Synthesis of 2,5-dibromoiodobenzene 2,5-Dibromoaniline 10 g was dispersed in diluted hydrochloric acid (concentrated hydrochloric acid 40 ml+water 30 ml), and an aqueous solution of $NaNO_2$ 3 g was dropwise added thereto at 0° C. The reaction solution was stirred for 40 minutes and then dropwise added at room temperature to an aqueous solution of potassium iodide 60 g which was separately prepared. After stirring at room temperature for 2 hours, methylene chloride and a small amount of sodium hydrogensulfite were added thereto, and the organic layer was extracted. The organic layer was washed with a 10% sodium hydrogensulfite aqueous solution and saturated brine and dried on anhydrous sodium sulfate, and then the solvent was distilled off. The product was refined by silica gel chromatography, whereby targeted 2,5-dibromoiodobenzene 10.5 g (yield: 73%) was obtained in the form of white crystal.

Synthetic Example 22

Synthesis of 10-(4-biphenyl) anthracene-9-boronic acid 10-(4-Biphenyl)anthracene-9-boronic acid was synthesized by the same method, except that in Synthetic Example 3, 4-bromobiphenyl was used as a starting material in place of 2-(4-bromophenyl)naphthalene.

Synthetic Example 23

Synthesis of 9-(2,5-dibromophenyl)-10-(4-biphenyl)anthracene 9-(2,5-Dibromophenyl)-10-(4-biphenyl)anthracene was synthesized by the same method, except that in Synthetic Example 3, 2,5-dibromoiodobenzene was used in place of 2-(4-bromophenyl)naphthalene and that 9-(4-biphenyl)anthracene-10-boronic acid was used in place of 9-anthraceneboronic acid.

Synthetic Example 24

Synthesis of 2-(5-bromo-2-methylphenyl)naphthalene

4-Bromo-2-iodotoluene was synthesized by the same method, except that in Synthetic Example 21, 5-bromo-2-methylaniline was used in place of 2,5-dibromoiodoaniline. Further, 2-(5-bromo-2-methylphenyl)naphthalene was synthesized by the same method, except that in Synthetic Example 1,4-bromo-2-iodotoluene was used in place of 4-bromoiodobenzene.

Synthetic Example 25

Synthesis of 9-bromo-2-t-butylanthracene

The same reaction was carried out using 2-t-butylanthracene in place of 9-(4-naphthalene-2-yl-phenyl)anthracene in Synthetic Example 4, and the product thus obtained was refined by silica gel chromatography, whereby 9-bromo-2-t-butylanthracene was synthesized.

Synthetic Example 26

Synthesis of 3-t-butyl-10-(4-naphthalene-2-yl-phenyl)anthracene-9-boronic acid 3-t-Butyl-10-(4-naphthalene-2-yl-phenyl)anthracene-9-boronic acid was synthesized by the same method using 9-bromo-2-t-butylanthracene as a starting material in place of 9-bromoanthracene in Synthetic Example 2.

Example 1

Synthesis of Compound AN-8

1-(4-Bromophenyl)naphthalene 4.0 g, 10-(4-naphthalene-2-yl-phenyl)anthracene-9-boronic acid 5.0 g and tetrakis (triphenylphosphine)palladium 0.41 g were mixed and substituted with argon. DME 100 ml and a 2M sodium carbonate aqueous solution 20 ml were added thereto, and the mixture was heated and refluxed for 10 hours.

After left cooling, deposited crystal was filtered and washed with water, methanol and toluene. The crystal thus obtained was recrystallized from toluene, filtered and dried, whereby the targeted compound (AN-8) 4.1 g was obtained in the form of pale yellow crystal (yield: 60%).

FD-MS (field desorption mass analysis) of the above compound gave m/z=582 versus $C_{46}H_{30}$=582.

Example 2

Synthesis of Compound AN-9

The targeted compound AN-9 was obtained in the form of cream-colored crystal (yield: 63%) by the same method, except that in Example 1, 9-(4-bromophenyl)phenanthrene was used in place of 1-(4-bromophenyl)naphthalene.

FD-MS of the above compound gave m/z=632 versus $C_{50}H_{32}$=632.

Example 3

Synthesis of Compound NA-45

The targeted compound AN-45 was obtained in the form of white crystal (yield: 50%) by the same method, except that in Example 1, 2-(3-bromophenyl)naphthalene was used in place of 1-(4-bromophenyl)naphthalene and that 10-(4-naphthalene-1-yl-phenyl)anthracene-9-boronic acid was used in place of 10-(4-naphthalene-2-yl-phenyl)anthracene-9-boronic acid.

FD-MS of the above compound gave m/z=582 versus $C_{46}H_{30}$=582.

Example 4

Synthesis of Compound AN-117

The targeted compound AN-117 was obtained in the form of pale yellow crystal (yield: 68%) by the same method, except that in Example 1, 2-(2-bromophenyl)naphthalene was used in place of 1-(4-bromophenyl)naphthalene and that 10-(4-naphthalene-1-yl-phenyl)anthracene-9-boronic acid was used in place of 10-(4-naphthalene-2-yl-phenyl)anthracene-9-boronic acid.

FD-MS of the above compound gave m/z=582 versus $C_{46}H_{30}$=582.

Example 5

Synthesis of Compound AN-144

The targeted compound AN-144 was obtained in the form of pale yellow crystal (yield: 44%) by the same method, except that in Example 1, 2-bromobiphenyl was used in place of 1-(4-bromophenyl)naphthalene and that 10-(4-naphthalene-1-yl-phenyl)anthracene-9-boronic acid was used in place of 10-(4-naphthalene-2-yl-phenyl)anthracene-9-boronic acid.

FD-MS of the above compound gave m/z=532 versus $C_{42}H_{28}$=532.

Example 6

Synthesis of Compound AN-145

The targeted compound AN-145 was obtained in the form of white crystal (yield: 53%) by the same method, except that in Example 1, 2-bromobiphenyl was used in place of 1-(4-bromophenyl)naphthalene.

FD-MS of the above compound gave m/z=532 versus $C_{42}H_{28}$=532.

Example 7

Synthesis of Compound AN-171

The targeted compound AN-171 was obtained in the form of pale yellow crystal (yield: 43%) by the same method, except that in Example 1, 2-bromo-p-terphenyl was used in place of 1-(4-bromophenyl)naphthalene and that 10-(4-naphthalene-1-yl-phenyl)anthracene-9-boronic acid was used in place of 10-(4-naphthalene-2-yl-phenyl)anthracene-9-boronic acid.

FD-MS of the above compound gave m/z=608 versus $C_{48}H_{32}$=608.

Example 8

Synthesis of Compound AN-179

The targeted compound AN-179 was obtained in the form of pale yellow crystal (yield: 48%) by the same method, except that in Example 1, 2-(4-bromophenyl)-p-terphenyl was used in place of 1-(4-bromophenyl)naphthalene and that 10-(p-terphenyl-2-yl)anthracene-9-boronic acid was used in place of 10-(4-naphthalene-2-yl-phenyl)anthracene-9-boronic acid.

FD-MS of the above compound gave m/z=710 versus $C_{56}H_{38}$=710.

Example 9

Synthesis of Compound AN-212

The targeted compound AN-212 was obtained in the form of white crystal (yield: 58%) by the same method, except that in Example 1, 1-(3-bromophenyl)naphthalene was used in place of 1-(4-bromophenyl)naphthalene and that 10-(biphenyl-2-yl)anthracene-9-boronic acid was used in place of 10-(4-naphthalene-2-yl-phenyl)anthracene-9-boronic acid.

FD-MS of the above compound gave m/z=532 versus $C_{42}H_{28}$=532.

Example 10

Synthesis of Compound AN-213

The targeted compound AN-213 was obtained in the form of pale yellow crystal (yield: 43%) by the same method, except that in Example 1, 2-(3-bromophenyl)naphthalene was used in place of 1-(4-bromophenyl)naphthalene and that 10-(biphenyl-2-yl)anthracene-9-boronic acid was used in place of 10-(4-naphthalene-2-yl-phenyl)anthracene-9-boronic acid.

FD-MS of the above compound gave m/z=532 versus $C_{42}H_{28}$=532.

Example 11

Synthesis of Compound AN-237

The targeted compound AN-237 was obtained in the form of white crystal (yield: 58%) by the same method, except that in Example 1, 2-(3-bromophenyl)naphthalene was used in place of 1-(4-bromophenyl)naphthalene and that 10-(p-terphenyl-2-yl)anthracene-9-boronic acid was used in place of 10-(4-naphthalene-2-yl-phenyl)anthracene-9-boronic acid. FD-MS of the above compound gave m/z=608 versus $C_{48}H_{32}$=608.

Example 12

Synthesis of Compound AN-251

The targeted compound AN-251 was obtained in the form of pale yellow crystal (yield: 58%) by the same method, except that in Example 1, 9-(3-bromophenyl)phenanthrene was used in place of 1-(4-bromophenyl)naphthalene and that 10-(3-naphthalene-2-yl-phenyl)anthracene-9-boronic acid was used in place of 10-(4-naphthalene-2-yl-phenyl)anthracene-9-boronic acid.

FD-MS of the above compound gave m/z=632 versus $C_{50}H_{32}$=632.

Example 13

Synthesis of Compound AN-275

The targeted compound AN-275 was obtained in the form of pale yellowish white crystal (yield: 45%) by the same method, except that in Example 1, 1-(2-bromophenyl)naphthalene was used in place of 1-(4-bromophenyl)naphthalene and that 10-(biphenyl-2-yl)anthracene-9-boronic acid was used in place of 10-(4-naphthalene-2-yl-phenyl)anthracene-9-boronic acid.

FD-MS of the above compound gave m/z=532 versus $C_{42}H_{28}$=532.

Example 14

Synthesis of Compound NA-281

The targeted compound NA-281 was obtained in the form of pale yellowish white crystal (yield: 48%) by the same method, except that in Example 1, 2-(2-bromophenyl)naphthalene was used in place of 1-(4-bromophenyl)naphthalene and that 10-(biphenyl-2-yl)anthracene-9-boronic acid was used in place of 10-(4-naphthalene-2-yl-phenyl)anthracene-9-boronic acid.

FD-MS of the above compound gave m/z=532 versus $C_{42}H_{28}$=532.

Example 15

Synthesis of Compound AN-296

The targeted compound AN-296 was obtained in the form of white crystal (yield: 35%) by the same method, except that in Example 1, 2-bromophenyl-p-terphenyl was used in place of 1-(4-bromophenyl)naphthalene and that 10-(biphenyl-2-yl)anthracene-9-boronic acid was used in place of 10-(4-naphthalene-2-yl-phenyl)anthracene-9-boronic acid.

FD-MS of the above compound gave m/z=558 versus $C_{44}H_{30}$=558.

Example 16

Synthesis of Compound AN-346

The targeted compound AN-346 was obtained in the form of pale yellow crystal (yield: 70%) by the same method, except that in Example 1, 2-(3-bromo-5-naphthalene-2-yl-phenyl)naphthalene was used in place of 1-(4-bromophenyl)naphthalene.

FD-MS of the above compound gave m/z=708 versus $C_{56}H_{36}$=708.

Example 17

Synthesis of Compound AN-358

The targeted compound AN-358 was obtained in the form of pale yellow crystal (yield: 62%) by the same method, except that in Example 1, 9-(2,5-dibromophenyl)-10-(4-biphenyl)anthracene was used in place of 1-(4-bromophenyl)naphthalene and that a twice amount of 1-naphthaleneboronic acid was used in place of 10-(4-naphthalene-2-yl-phenyl)anthracene-9-boronic acid.

FD-MS of the above compound gave m/z=658 versus $C_{52}H_{34}$=658.

Example 18

Synthesis of Compound AN-393

The targeted compound AN-393 was obtained in the form of pale yellow crystal (yield: 64%) by the same method, except that in Example 1, 2-(5-bromo-2-methylphenyl)naphthalene was used in place of 1-(4-bromophenyl)naphthalene.

FD-MS of the above compound gave m/z=596 versus $C_{47}H_{32}$=596.

Example 19

Synthesis of Compound AN-402

The targeted compound AN-402 was obtained in the form of pale yellow crystal (yield: 42%) by the same method, except that in Example 1, 2-bromobiphenyl was used in place of 1-(4-bromophenyl)naphthalene and that 3-t-butyl-10-(4-naphthalene-2-yl-phenyl)anthracene-9-boronic acid was used in place of 10-(4-naphthalene-2-yl-phenyl)anthracene-9-boronic acid.

FD-MS of the above compound gave m/z=588 versus $C_{46}H_{36}$=588.

Example 20

Production of organic EL device

A glass substrate (manufactured by Geomatech Co., Ltd.) of 25 mm×75 mm×1.1 mm thickness equipped with an ITO transparent electrode was subjected to supersonic wave washing in isopropyl alcohol for 5 minutes and then to UV ozone washing for 30 minutes. After washed, the glass substrate equipped with an ITO transparent electrode line was loaded in a substrate holder of a vacuum deposition apparatus, and a N,N'-bis(N,N'-diphenyl-4-aminophenyl)-N,N-diphenyl-4,4'-diamino-1,1'-biphenyl film (hereinafter referred to as a TPD 232 film) shown below having a film thickness of 60 nm was formed on a face of a side at which the transparent electrode line was formed so that it covered the transparent electrode described above. This TPD 232 film functions as a hole injecting layer. Next, the following N,N,N',N'-tetra(4-biphenyl)-diaminobiphenylene film (hereinafter referred to as a TBDB film) having a film thickness of 20 nm was formed on the above TPD 232 film. This film functions as a hole transporting layer. Further, the compound AN-8 described above was deposited to form a film having a film thickness of 40 nm. At the same time, the following amine compound D1 having a styryl group was deposited as a luminescent material in a weight ratio of AN-8 to D1=40:3. This film functions as a luminescent layer. An Alq film having a film thickness of 10 nm was formed on the above film. This film functions as an electron injecting layer. Then, Li (Li source: manufactured by Saesgetter Co., Ltd.) which was a reducing dopant and the following Alq were subjected to binary deposition to form an Alq:Li film (film thickness: 10 nm) as an electron injecting layer (or cathode). Metal Al was deposited on the above Alq:Li film to form a metal cathode, whereby an organic EL device was formed.

The depositing temperature (deposition source temperature at a depositing speed of 1 Å/sec) in forming the luminescent layer was 300° C. Further, a luminous efficiency of the organic EL device obtained was measured, and a change in the luminance at an initial luminance of 1000 nit was measured to find that the luminance after 2443 hours passed since starting observation was 712 nit and that the measurement result of a half life of the above device was 6050 hours.

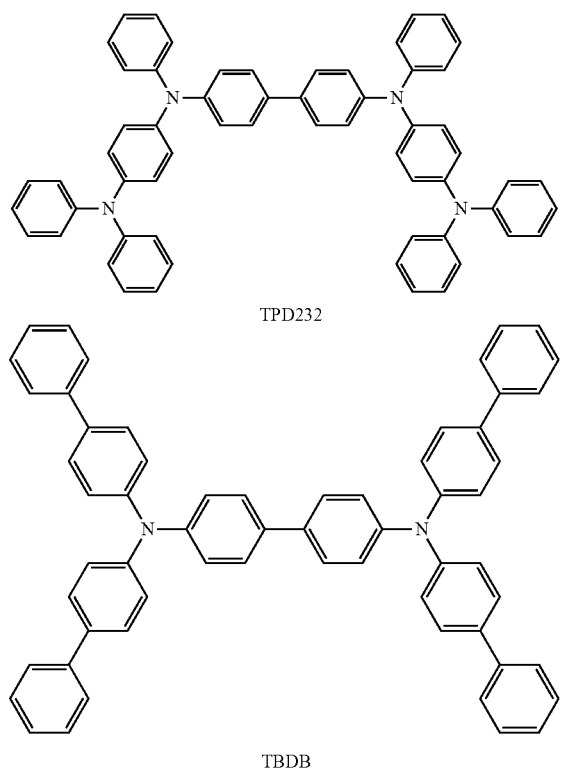

TPD232

TBDB

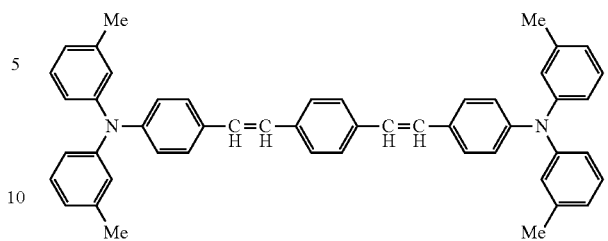

D1

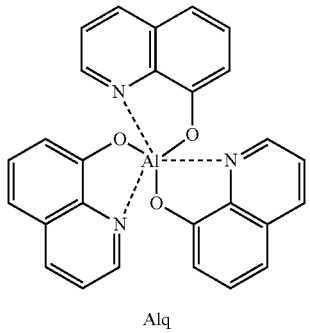

Alq

Examples 21 to 22

Organic EL devices were prepared in the same manner, except that in Example 20, compounds described in Table 1 were used as materials for the luminescent layers in place of the compound AN-8.

Further, measured in the same manner as in Example 20 were the depositing temperatures in forming the luminescent layers, the luminous efficiencies of the organic EL devices obtained and the half lives at an initial luminance of 1000 nit, and the results thereof are shown in Table 1.

Example 23

An organic EL device was prepared in the same manner, except that in Example 20, the following amine compound D2 was used as a material for the luminescent layer in place of the amine compound D1.

Further, measured in the same manner as in Example 20 were the depositing temperature in forming the luminescent layer, a luminous efficiency of the organic EL device obtained and the half life at an initial luminance of 1000 nit, and the results thereof are shown in Table 1.

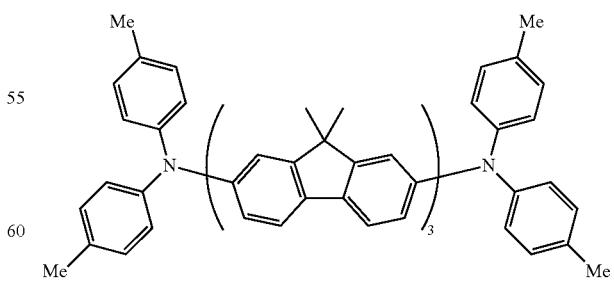

D2

Examples 24 to 26

Organic EL devices were prepared in the same manner, except that in Example 20, AN-45, AN-72 and AN-74 each were used, as described in Table 1, as materials for the luminescent layers in place of the compound AN-8.

Further, measured in the same manner as in Example 20 were the depositing temperatures in forming the luminescent layers, the luminous efficiencies of the organic EL devices obtained and the half lives at an initial luminance of 1000 nit, and the results thereof are shown in Table 1.

Comparative Examples 1 to 3

Organic EL devices were prepared in the same manner, except that in Example 20, the compounds described below and in Table 1 were used as materials for the luminescent layers in place of the compound AN-8.

Further, measured in the same manner as in Example 20 were the depositing temperatures in forming the luminescent layers, the luminous efficiencies of the organic EL devices obtained and the half lives at an initial luminance of 1000 nit, and the results thereof are shown in Table 1.

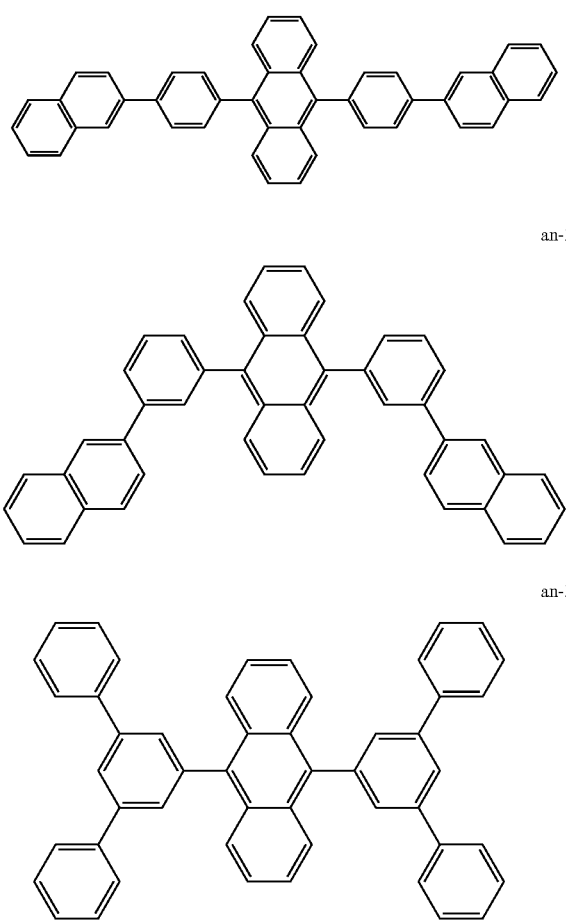

TABLE 1

|  | Compound in luminescent layer | Luminous efficiency (cd/A) | Half life (hour) | Depositing temperature (° C.) |
| --- | --- | --- | --- | --- |
| Example 20 | AN-8/D1 | 11.1 | 6,050 | 300 |
| Example 21 | AN-213/D1 | 10.9 | 4,000 | 261 |
| Example 22 | AN-346/D1 | 10.7 | 3,300 | 254 |
| Example 23 | AN-8/D2 | 10.5 | 3,800 | 300 |
| Example 24 | AN-45/D1 | 11.2 | 6,200 | 298 |
| Example 25 | AN-72/D1 | 10.9 | 4,000 | 262 |
| Example 26 | AN-74/D1 | 11.0 | 5800 | 305 |
| Comparative Example 1 | an-1/D1 | 8.7 | 900 | 349 |
| Comparative Example 2 | an-2/D1 | 8.7 | 800 | 331 |
| Comparative Example 3 | an-3/D1 | 8.9 | 500 | 310 |

INDUSTRIAL APPLICABILITY

As explained above in details, an organic EL device prepared by using a material for an organic EL device comprising the asymmetric monoanthracene derivative of the present invention represented by Formula (1) has a high luminous efficiency and a long life. Accordingly, it is useful as an organic EL device which is assumed to be continuously used over a long period of time. Further, use of the compound having a monoanthracene structure of an asymmetric type represented by the following Formula (1) as a material for an organic EL device makes it possible to lower a depositing temperature of the compound and inhibits the compound from being thermally decomposed in deposition.

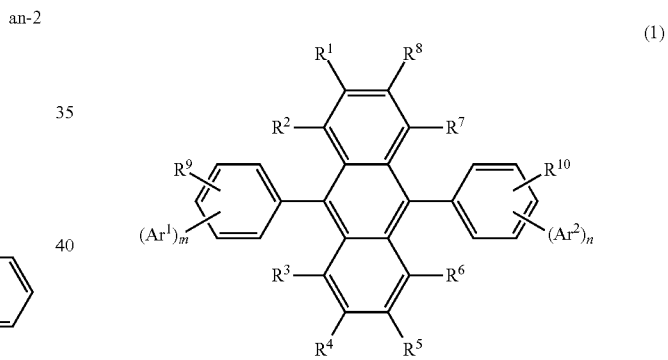

What is claimed is:
1. An asymmetric monoanthracene derivative represented by the following Formula (2):

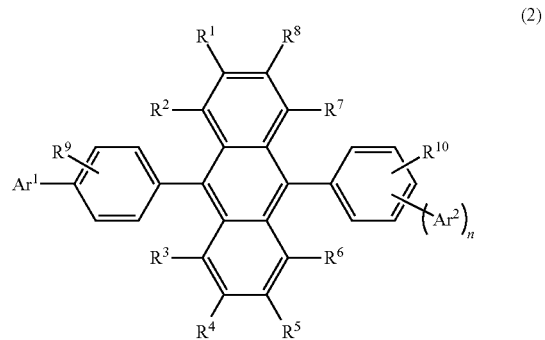

wherein $Ar^1$ and $Ar^2$ each are independently a substituted or non-substituted aromatic hydrocarbon ring selected from the group consisting of phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 1-naphthacenyl, 2-naphthacenyl, 9-naphthacenyl, 1-pyrenyl, 2-pyrenyl, 4-pyrenyl, 2-biphenylyl, 3-biphenylyl, 4-biphenylyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-t-butylphenyl, p-(2-phenylpropyl)phenyl, 3-methyl-2-naphthyl, 4-methyl-1-naphthyl, 4-methyl-1-anthryl, 4'-methylbiphenylyl and 4"-t-butyl-p-terphenyl-4-yl, provided that when Ar$^1$ or Ar$^2$ is a phenyl group, the phenyl group has no substituents, Ar$^2$ has an ortho bonding position or meta bonding position, and n is an integer of 1 to 4;

R$^1$ to R$^8$ each are independently a hydrogen atom, a substituted or non-substituted aromatic hydrocarbon ring group having 6 to 50 nuclear carbon atoms, a substituted or non-substituted aromatic heterocyclic group having 5 to 50 nuclear atoms, a substituted or non-substituted alkyl group having 1 to 50 carbon atoms, a substituted or non-substituted cycloalkyl group, a substituted or non-substituted alkoxy group having 1 to 50 carbon atoms, a substituted or non-substituted aralkyl group having 6 to 50 carbon atoms, a substituted or non-substituted aryloxy group having 5 to 50 nuclear atoms, a substituted or non-substituted arylthio group having 5 to 50 nuclear atoms, a substituted or non-substituted alkoxycarbonyl group having 1 to 50 carbon atoms, a substituted or non-substituted silyl group, a carboxyl group, a halogen atom, a cyano group, a nitro group or a hydroxyl group; and R$^9$ and R$^{10}$ each are independently a hydrogen atom, a substituted or non-substituted aromatic hydrocarbon ring selected from the group consisting of phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 1-naphthacenyl, 2-naphthacenyl, 9-naphthacenyl,1-pyrenyl, 2-pyrenyl, 4-pyrenyl, 2-biphenylyl, 3-biphenylyl, 4-biphenylyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-t-butylphenyl, p-(2-phenylpropyl)phenyl, 3-methyl-2-naphthyl, 4-methyl-1-naphthyl, 4-methyl-1-anthryl, 4'-methylbiphenylyl and 4"-t-butyl-p-terphenyl-4-yl, a substituted or non-substituted alkyl group having 1 to 50 carbon atoms, a substituted or non-substituted cycloalkyl group, a substituted or non-substituted alkoxy group having 1 to 50 carbon atoms, a substituted or non-substituted aralkyl group having 6 to 50 carbon atoms, a substituted or non-substituted aryloxy aroup having 5 to 50 nuclear atoms, a substituted or non-substituted arylthio group having 5 to 50 nuclear atoms, a substituted or non-substituted alkoxycarbonyl group having 1 to 50 carbon atoms, a substituted or non-substituted silyl group, a carboxyl group, a halogen atom, a cyano group, a nitro group or a hydroxyl group, and any groups are not an alkenyl group.

2. An asymmetric monoanthracene derivative represented by the following Formula (4):

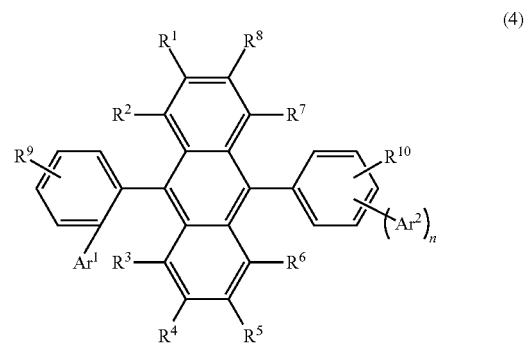

(4)

Ar$^1$ and Ar$^2$ each are independently a substituted or non-substituted aromatic hydrocarbon ring selected from the group consisting of phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 1-naphthacenyl, 2-naphthacenyl, 9-naphthacenyl, 1-pyrenyl, 2-pyrenyl, 4-pyrenyl, 2-biphenylyl, 3-biphenylyl, 4-biphenylyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-t-butylphenyl, p-(2-phenylpropyl)phenyl, 3-methyl-2-naphthyl, 4-methyl- 1-naphthyl, 4-methyl-1-anthryl, 4'-methylbiphenylyl and 4"-t-butyl-p-terphenyl-4-yl, Ar$^2$ has a meta bonding positon or para bonding position, and n is an integer of 1 to 3, provided that when Ar$^1$ or Ar$^2$ is a phenyl group, the phenyl group has no substituents;

R$^1$ to R$^8$ each are independently a hydrogen atom, a substituted or non-substituted aromatic hydrocarbon ring group having 6 to 50 nuclear carbon atoms, a substituted or non-substituted aromatic heterocyclic group having 5 to 50 nuclear atoms, a substituted or non-substituted alkyl group having 1 to 50 carbon atoms, a substituted or non-substituted cycloalkyl group, a substituted or non-substituted alkoxy group having 1 to 50 carbon atoms, a substituted or non-substituted aralkyl group having 6 to 50 carbon atoms, a substituted or non-substituted aryloxy group having 5 to 50 nuclear atoms, a substituted or non-substituted arylthio group having 5 to 50 nuclear atoms, a substituted or non-substituted alkoxycarbonyl group having 1 to 50 carbon atoms, a substituted or non-substituted silyl group, a carboxyl group, a halogen atom, a cyano group, a nitro group or a hydroxyl group; and R$^9$ and R$^{10}$ each are independently a hydrogen atom, a substituted or non-substituted aromatic hydrocarbon ring selected from the group consisting of phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 1-naphthacenyl, 2-naphthacenyl, 9-naphthacenyl,1-pyrenyl, 2-pyrenyl, 4-pyrenyl, 2-biphenylyl, 3-biphenylyl, 4-biphenylyl, p-terphenyl-4-yl, p-terphenyl-3-yl, p-terphenyl-2-yl, m-terphenyl-4-yl, m-terphenyl-3-yl, m-telphenyl-2-yl, o-tolyl, p-tolyl, p-t-butylphenyl, p-(2-phenylpropyl)phenyl, 3-methyl-2-naphthyl, 4-methyl-1-naphthyl, 4-methyl-1-anthryl, 4'-methylbiphenylyl and 4"-t-butyl-p-terphenyl-4-yl, a substituted or non-substituted alkyl group having 1 to 50 carbon atoms, a substituted or non-substituted, cycloalkyl group, a substituted or non-substituted alkoxy group having 1 to 50 carbon atoms, a substituted or non-substituted aralkyl group having 6 to 50 carbon atoms, a substituted or non-substituted aryloxy group having 5 to 50 nuclear atoms, a substituted or non-substituted arylthio group having 5 to 50 nuclear atoms, a substituted or non-substituted alkoxycarbonyl group having 1 to 50 carbon atoms, a substituted or non-substituted silyl group, a carboxyl group, a halogen atom, a cyano group, a nitro group or a hydroxyl group, and any groups are not an alkenyl group.

3. The asymmetric monoanthracene derivative represented by Formula (2) as described in claim 1, wherein $Ar^1$ and $Ar^2$ are each independently selected from the group consisting of phenyl, 1-naphthyl, 2-naphthyl, 9-phenanthryl, 1-naphthacenyl, 2-naphthacenyl, 9-naphthacenyl, 1-pyrenyl, 2-pyrenyl, 4-pyrenyl, 2-biphenylyl, 3-biphenylyl, o-tolyl, m-tolyl, p-tolyl and p-t-butylphenyl.

4. The asymmetric monoanthracene derivative represented by Formula (4) as described in claim 2, wherein $Ar^1$ and $Ar^2$ are each independently selected from the group consisting of phenyl, 1-naphthyl, 2-naphthyl, 9-phenanathryl, 1-naphthacenyl, 2-naphthacenyl, 9-naphthacenyl, 1-pyrenyl, 2-pyranyl, 4-pyrenyl, 2-biphenylyl, 3-biphenylyl, 4-biphenylyl, o-tolyl, m-tolyl, p-tolyl and p-t-butylphenyl.

5. The asymmetric monoanthracene derivative represented by Formula (2) as described in claim 1, wherein $Ar^2$ has an ortho bonding position.

6. The asymmetric monoanthracene derivative represented by Formula (2) as described in claim 1, wherein $Ar^2$ has a meta bonding position.

7. The asymmetric monoanthracene derivative represented by Formula (4) as described in claim 2, wherein $Ar^2$ has a meta bonding position.

8. The asymmetric monoanthracene derivative represented by Formula (4) as described in claim 2, wherein $Ar^2$ has a para bonding position.

9. The asymmetric monoanthracene derivative represented by Formula (2) as described in claim 1, wherein $Ar^1$ and $Ar^2$ are each independently selected from the group consisting of phenyl, 1-naphthyl, 2-naphthyl, and 9,-phenanthryl.

10. The asymmetric monoanthracene derivative represented by Formula (4) as described in claim 2, wherein $Ar^1$ and $Ar^2$ are each independently selected from the group consisting of phenyl, 1-naphthyl, 2-naphthyl, and 9-phenanthryl.

11. The asymmetric monoanthracene derivative represented by Formula (2) as described in claim 1, wherein $R^9$ and $R^{10}$ are independently a hydrogen atom.

12. The asymmetric monoanthracene derivative represented by Formula (4) as described in claim 2, wherein $R^9$ and $R^{10}$ are independently a hydrogen atom.

13. ; The asymmetric monoanthracene derivative represented by Formula (2) as described in claim 1, wherein n is 1.

14. The asymmetric monoanthracene derivative represented by Formula (4) as described in claim 2, wherein n is 1.

15. The asymmetric monoanthracene derivative represented by Formula (2) as described in claim 1, wherein $Ar^1$ and $Ar^2$ are each independently a substituted or non-substituted aromatic hydrocarbon ring selected from the group consisting of a phenyl group, a naphthyl group, a phenanthryl group, a biphenylyl group, and a terphenylyl group;
$R^9$ and $R^{10}$ are a hydrogen atom;
$R^1$-$R^8$ are independently a hydrogen atom or a substituted or non-substituted aromatic hydrocarbon ring group having 6 to 50 nuclear carbon atoms; and
n is 1.

16. The asymmetric monoanthracene derivative represented by Formula (4) as described in claim 2, wherein $Ar^1$ and $Ar^2$ are each independently a substituted or non-substituted aromatic hydrocarbon ring selected from the group consisting of a phenyl group, a naphthyl group, a phenanthryl group, a biphenylyl group, and a terphenylyl group;
$R^9$ and $R^{10}$ are a hydrogen atom;
$R^1$-$R^8$ are independently a hydrogen atom or a substituted or non-substituted aromatic hydrocarbon ring group having 6 to 50 nuclear carbon atoms; and
n is 1.

17. The asymmetric monoanthracene derivative represented by Formula (2) as described in claim 1, wherein $Ar^1$ and $Ar^2$ are each independently a substituted or non-substituted aromatic hydrocarbon ring selected from the group consisting of phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 2-biphenylyl, 3-biphenylyl, 4-biphenylyl, p-terphenyl-4-yl, p-terphenyl-3-yl, p-terphenyl-2-yl, m-terphenyl-4-yl, m-terphenyl-3-yl, m-terpheriyl-2-yl, 4'-methylbiphenylyl and 4"-t-butyl-p-terphenyl-4-yl;
$R^9$ and $R^{10}$ are a hydrogen atom;
$R^1$-$R^8$ are independently a hydrogen atom or a substituted or non-substituted aromatic hydrocarbon ring group having 6 to 50 nuclear carbon atoms; and
n is 1.

18. The asymmetric monoanthracene derivative represented by Formula (4) as described in claim 2, wherein $Ar^1$ and $Ar^2$ are each independently a substituted or non-substituted aromatic hydrocarbon ring selected from the group consisting of phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 2-biphenylyl, 3-biphenylyl, 4-biphenylyl, p-terphenyl-4-yl, p-terphenyl-3-yl, p-terphenyl-2-yl, m-terphenyl-4-yl, m-terphenyl-3-yl, m-terphenyl-2-yl, 4'-methylbiphenylyl and 4"-t-butyl-p-terphenyl-4-yl;
$R^9$ and $R^{10}$ are a hydrogen atom;
$R^1$-$R^8$ are independently a hydrogen atom or a substituted or non-substituted aromatic hydrocarbon ring group having 6 to 50 nuclear carbon atoms; and
n is 1.

* * * * *